(12) United States Patent
Liu et al.

(10) Patent No.: US 11,713,452 B2
(45) Date of Patent: Aug. 1, 2023

(54) ENGINEERED CAS9 VARIANTS

(71) Applicant: UNIVERSITY OF NORTH TEXAS HEALTH SCIENCE CENTER, Ft. Worth, TX (US)

(72) Inventors: Jin Liu, Ft. Worth, TX (US); Zhicheng Zuo, Ft. Worth, TX (US); Yu-Chieh Wang, Ft. Worth, TX (US)

(73) Assignee: UNIVERSITY OF NORTH TEXAS HEALTH SCIENCE CENTER, Ft. Worth, TX (US)

( * ) Notice: Subject to any disclaimer, the term of this patent is extended or adjusted under 35 U.S.C. 154(b) by 474 days.

(21) Appl. No.: 16/645,254

(22) PCT Filed: Sep. 10, 2018

(86) PCT No.: PCT/US2018/050279
§ 371 (c)(1),
(2) Date: Mar. 6, 2020

(87) PCT Pub. No.: WO2019/051419
PCT Pub. Date: Mar. 14, 2019

(65) Prior Publication Data
US 2020/0208129 A1    Jul. 2, 2020

Related U.S. Application Data

(60) Provisional application No. 62/555,873, filed on Sep. 8, 2017.

(51) Int. Cl.
| | |
|---|---|
| *C12N 9/22* | (2006.01) |
| *G16B 15/00* | (2019.01) |
| *G16B 5/00* | (2019.01) |
| *G06F 30/20* | (2020.01) |
| *C12N 15/11* | (2006.01) |
| *G06F 17/16* | (2006.01) |
| *G06F 111/10* | (2020.01) |

(52) U.S. Cl.
CPC ............... *C12N 9/22* (2013.01); *C12N 15/11* (2013.01); *G06F 17/16* (2013.01); *G06F 30/20* (2020.01); *G16B 5/00* (2019.02); *G16B 15/00* (2019.02); *C12N 2800/80* (2013.01); *G06F 2111/10* (2020.01)

(58) Field of Classification Search
CPC ....................................................... C12N 9/22
See application file for complete search history.

(56) References Cited

U.S. PATENT DOCUMENTS

| | | | |
|---|---|---|---|
| 2014/0186919 A1 | 7/2014 | Zhang et al. | |
| 2014/0273226 A1 | 9/2014 | Wu | |
| 2015/0284727 A1 | 10/2015 | Kim et al. | |
| 2016/0362667 A1* | 12/2016 | Donohoue | C12N 9/22 |
| 2017/0058271 A1* | 3/2017 | Joung | C12Y 301/00 |
| 2018/0100148 A1* | 4/2018 | Vakulskas | C12N 15/11 |
| 2019/0010471 A1* | 1/2019 | Zhang | C12Y 301/00 |
| 2020/0149022 A1* | 5/2020 | Kim | C12N 15/102 |

FOREIGN PATENT DOCUMENTS

| | | | |
|---|---|---|---|
| WO | WO 2016115355 | * | 7/2016 |
| WO | WO2016/205613 | * | 12/2016 |
| WO | WO 2018226855 | * | 12/2018 |
| WO | WO 2018074979 | * | 4/2019 |

OTHER PUBLICATIONS

Anders, et al. "Structural basis of PAM-dependent target DNA recognition by the Cas9 endonuclease," *Nature*, 2014, 513(7519):569-573.
Biertumpfel, et al. "Crystal structure of T4 endonuclease VII resolving a Holliday junction," *Nature*, 2007, 449(7162):616-620.
Charpentier, et al. "Rewriting a genome," *Nature*, 2013, 495:50-51.
Cong, et al. "Multiplex Genome Engineering Using CRISPR/Cas Systems," *Science*, 2013, 339(6121):819-823.
Dagdas, et al. "A conformational checkpoint between DNA binding and cleavage by CRISPR-Cas9," *bioRxiv*, 2017,122242.
Gasiunas, et al. "Cas9-crRNA ribonucleoprotein complex mediates specific DNA cleavage for adaptive immunity in bacteria," *Proceedings of the National Academy of Sciences of the U.S.A.*, 2012, 109(39):E2579-2586.
Gordon, et al. "H++: A Server for Estimating pKas and Adding Missing Hydrogens to Macromolecules," *Nucleic Acids Research*, 2005, 33:W368-371.
Heler, et al. "Mutations in Cas9 Enhance the Rate of Acquisition of Viral Spacer Sequences during the CRISPR-Cas Immune Response," *Molecular Cell*, 2017, 65(1):168-175.
International Search Report and Written Opinion issued in International Patent Application No. PCT/US2018/050279, dated Jan. 28, 2019.
Jiang, et al. "A Cas9-guide RNA complex preorganized for target DNA recognition," *Science*, 2015, 348(6242):1477-1481.
Jiang, et al. "CRISPR-Cas9 Structures and Mechanisms," *Annual Review of Biophysics*, 2017, 46:505-529.
Jiang, et al. "Structures of a CRISPR-Cas9 R-loop complex primed forvDNA cleavage," *Science*, 2016, 351:867-871.
Jinek, et al. "A Programmable Dual-RNA-Guided DNA Endonuclease in Adaptive Bacterial Immunity," *Science*, 2012, 337:816-821.
Jinek, et al. "Structures of Cas9 Endonucleases Reveal RNA-Mediated Conformational Activation," *Science*, 2014, 343(6176):1247997.
Kleinstiver, et al. "High-fidelity CRISPR-Cas9 Nucleases With No Detectable Genome-Wide Off-Target Effects," *Nature*, 2016, 529(7587):490-495.

(Continued)

*Primary Examiner* — Suzanne M Noakes
(74) *Attorney, Agent, or Firm* — Norton Rose Fulbright US LLP

(57) ABSTRACT

Certain embodiments are directed to modified or variant Cas9 proteins, and/or methods of using the same.

16 Claims, 13 Drawing Sheets
Specification includes a Sequence Listing.

(56) References Cited

OTHER PUBLICATIONS

Mali, et al. "RNA-Guided Human Genome Engineering via Cas9," *Science*, 2013, 339(6121):823-826.

Nguyen, et al. "CLICK—topology-independent comparison of biomolecular 3D structures," *Nucleic Acids Research*, 2011, 39:W24-W28.

Nishimasu, et al. "Crystal Structure of Cas9 in Complex with Guide RNA and Target DNA," *Cell*, 2014, 156(5):935-949.

Palermo, et al. "CRISPR-Cas9 conformational activation as elucidated from enhanced molecular simulations," *Proceedings of the National Academy of Sciences of the U.S.A.*, 2017, 114(28):7260-7265.

Palermo, et al. "Striking Plasticity of CRISPR-Cas9 and Key Role of Non-target DNA, as Revealed by Molecular Simulations," *ACS Central Science*, 2016, 2(10):756-763.

Reyon, et al. "FLASH Assembly of TALENs for High-Throughput Genome Editing," *Nature Biotechnology*, 2012, 30(5):460-465.

Salomon-Ferrer, et al. "An overview of the Amber biomolecular simulation package," *WIREs Computational Molecular Science*, 2013, 3:198-210.

Schaefer, et al. "Unexpected Mutations After CRISPR-Cas9 Editing in Vivo," *Nature Methods*, 2017, 14(6):547-548.

Shannon, "Revised effective ionic radii and systematic studies of interatomic distances in halides and chalcogenides," *Acta crystallographica section A: crystal physics, diffraction, theoretical and general crystallography*, 1976, 32:751-767.

Slaymaker, et al. "Rationally Engineered Cas9 Nucleases With Improved Specificity," *Science*, 2016, 351(6268):84-88.

Sternberg, et al. "DNA Interrogation by the CRISPR RNA-guided Endonuclease Cas9," *Nature*, 2014, 507(7490):62-67.

Yang, "An Equivalent Metal Ion In One- and Two-metal Ion Catalysis," *Nature Structural & Molecular. Biology*, 2008, 15(11):1228-1231.

Yang, "Nucleases: Diversity of Structure, Function and Mechanism," *Quarterly Reviews of Biophysics*, 2011, 44(1):1-93.

Yang, et al. "Making and Breaking Nucleic Acids: two-Mg2+-ion Catalysis and Substrate Specificity," *Molecular Cell*, 2006, 7(22):5-13.

Zuo, et al. "Cas9-catalyzed DNA Cleavage Generates Staggered Ends: Evidence from Molecular Dynamics Simulations," *Scientific Reports*, 2016, 5:37584.

\* cited by examiner

SEQUENCE LISTING

<160> NUMBER OF SEQ ID NOS: 1

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
```

-continued

```
              785                 790                 795                 800
Val Glu Asn Thr Gln Leu Gln Asn Gly Lys Leu Tyr Leu Tyr Tyr Leu
                        805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
                1010                1015                1020

Lys Ser Glu Gln Glu Ile Gly Lys Ala Thr Ala Lys Tyr Phe Phe
                1025                1030                1035

Tyr Ser Asn Ile Met Asn Phe Phe Lys Thr Glu Ile Thr Leu Ala
                1040                1045                1050

Asn Gly Glu Ile Arg Lys Arg Pro Leu Ile Glu Thr Asn Gly Glu
                1055                1060                1065

Thr Gly Glu Ile Val Trp Asp Lys Gly Arg Asp Phe Ala Thr Val
                1070                1075                1080

Arg Lys Val Leu Ser Met Pro Gln Val Asn Ile Val Lys Lys Thr
                1085                1090                1095

Glu Val Gln Thr Gly Gly Phe Ser Lys Glu Ser Ile Leu Pro Lys
                1100                1105                1110

Arg Asn Ser Asp Lys Leu Ile Ala Arg Lys Lys Asp Trp Asp Pro
                1115                1120                1125

Lys Lys Tyr Gly Gly Phe Asp Ser Pro Thr Val Ala Tyr Ser Val
                1130                1135                1140

Leu Val Val Ala Lys Val Glu Lys Gly Lys Ser Lys Lys Leu Lys
                1145                1150                1155

Ser Val Lys Glu Leu Leu Gly Ile Thr Ile Met Glu Arg Ser Ser
                1160                1165                1170

Phe Glu Lys Asn Pro Ile Asp Phe Leu Glu Ala Lys Gly Tyr Lys
                1175                1180                1185

Glu Val Lys Lys Asp Leu Ile Ile Lys Leu Pro Lys Tyr Ser Leu
                1190                1195                1200
```

-continued

```
Phe Glu Leu Glu Asn Gly Arg Lys Arg Met Leu Ala Ser Ala Gly
    1205              1210              1215

Glu Leu Gln Lys Gly Asn Glu Leu Ala Leu Pro Ser Lys Tyr Val
    1220              1225              1230

Asn Phe Leu Tyr Leu Ala Ser His Tyr Glu Lys Leu Lys Gly Ser
    1235              1240              1245

Pro Glu Asp Asn Glu Gln Lys Gln Leu Phe Val Glu Gln His Lys
    1250              1255              1260

His Tyr Leu Asp Glu Ile Ile Glu Gln Ile Ser Glu Phe Ser Lys
    1265              1270              1275

Arg Val Ile Leu Ala Asp Ala Asn Leu Asp Lys Val Leu Ser Ala
    1280              1285              1290

Tyr Asn Lys His Arg Asp Lys Pro Ile Arg Glu Gln Ala Glu Asn
    1295              1300              1305

Ile Ile His Leu Phe Thr Leu Thr Asn Leu Gly Ala Pro Ala Ala
    1310              1315              1320

Phe Lys Tyr Phe Asp Thr Thr Ile Asp Arg Lys Arg Tyr Thr Ser
    1325              1330              1335

Thr Lys Glu Val Leu Asp Ala Thr Leu Ile His Gln Ser Ile Thr
    1340              1345              1350

Gly Leu Tyr Glu Thr Arg Ile Asp Leu Ser Gln Leu Gly Gly Asp
    1355              1360              1365
```

ENGINEERED CAS9 VARIANTS

CROSS REFERENCE TO RELATED APPLICATIONS

This application is a national phase under 35 U.S.C. § 371 of International Application No. PCT/US2018/050279, filed Sep. 10, 2018, which claims the benefit of priority to U.S. Provisional Patent Application Ser. No. 62/555,873, filed Sep. 8, 2017, the entire contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 8, 2017, is named "99533996_1.txt" and is 12,121 bytes in size.

BACKGROUND OF THE INVENTION

A. Field of the Invention

The invention generally concerns an engineered Cas9 protein and method for producing and/or using the same.

B. Description of Related Art

The Clustered Regularly Interspaced Short Palindromic Repeats (CRISPR)/CRISPR-associated protein 9 (Cas9) system from *Streptococcus pyogenes* has recently been repurposed as a powerful and versatile genome-editing toolbox used in various living cells and organisms, demonstrating an enormous potential toward future therapeutic applications (Jiang and Doudna, *Annu. Rev. Biophys.,* 2017; Charpentier and Doudna, *Nature* 495, 50-51, 2013; Mali et al. *Science* 339, 823-26, 2013; Cong et al. *Science* 339, 819-23, 2013). Guided by a chimeric single-guide RNA (sgRNA), the endonuclease Cas9 generates site-specific breaks in the double-stranded DNA (dsDNA) target (Jinek et al. *Science* 337, 816-21, 2012; Gasiunas et al. *Proc. Natl. Acad. Sci. U.S.A.* 109, E2579-86, 2012). Recognition and cleavage of dsDNA strictly require the presence of a protospacer adjacent motif (PAM) in the non-target DNA strand (ntDNA) and depend on the base-pair complementarity of the target DNA strand (tDNA) to the RNA guide template (Jinek et al. *Science* 337, 816-21, 2012; Gasiunas et al. *Proc. Natl. Acad. Sci. U.S.A.* 109, E2579-86, 2012). Cas9 adopts an overall bi-lobed architecture, in which the sgRNA:tDNA heteroduplex resides within the central channel between the α-helical recognition (REC) and nuclease (NUC) lobes, while the displaced ntDNA threads into a side channel within the NUC lobe (FIG. 7) (Jiang et al. *Science* 351, 867-71, 2016; Jiang et al. *Science* 348, 1477-81, 2015; Nishimasu et al. *Cell* 156, 935-49, 2014; Anders et al. *Nature* 513, 569-73, 2014). The NUC lobe comprises of two metal-ion-dependent nuclease domains, dubbed as HNH and RuvC, which are responsible for cutting the tDNA (via one-metal-ion mechanism) (Yang, *Q. Rev. Biophys.* 44, 1-93, 2011; Yang, *Nat. Struct. Mol. Biol.* 15, 1228-31, 2008) and ntDNA (via two-metal-ion mechanism (Yang, *Q. Rev. Biophys.* 44, 1-93, 2011; Yang, *Nat. Struct. Mol. Biol.* 15, 1228-31, 2008; Yang et al., *Mol. Cell* 22, 5-13, 2006), respectively.

Capturing catalytic metal ion-containing nuclease/substrate complexes has been nontrivial for experimental means like X-ray crystallography and NMR spectroscopy, as the reaction generally occurs instantly (Yang et al., *Mol. Cell* 22, 5-13, 2006). It is thus not surprising that none of the Cas9 crystal structures in different binding forms solved over the past few years assumes a fully active state for either RuvC or HNH domain (Jiang et al. *Science* 351, 867-71, 2016; Jiang et al. *Science* 348, 1477-81, 2015; Nishimasu et al. *Cell* 156, 935-49, 2014; Anders et al. *Nature* 513, 569-73, 2014; Jinek et al. *Science* 343, 1247997, 2014).

In the inventors' recent work, using molecular dynamics simulations, the catalytically competent state of RuvC domain primed for cleaving the ntDNA was reported (Zuo and Liu, *Sci. Rep.* 5, 2016). However, the inventors were unable to capture the catalytic conformation of the HNH domain for cleaving the tDNA in the previous study (Zuo and Liu, *Sci. Rep.* 5, 2016). In contrast with the RuvC domain, the active center of HNH domain is surprisingly distant from the scissile phosphate on the tDNA in all available structures (Jiang et al. *Science* 351, 867-71, 2016; Jiang et al. *Science* 348, 1477-81, 2015; Nishimasu et al. *Cell* 156, 935-49, 2014; Anders et al. *Nature* 513, 569-73, 2014), with a separation of ~13 Å in the complete DNA duplex bound pre-catalytic state (FIG. 7*a*-7*b*) to ~46 Å in the RNA-only bound inactive state. In this respect, how to obtain a reliable catalytic state of Cas9 HNH domain has been of special focus to the experimental biologists and the computational biophysicists, as this structure can bridge one important missing link in understanding Cas9 binding, activation and cleavage mechanism and guides structure-based Cas9 engineering with enhanced specificity (Slaymaker et al. *Science* 351, 84-88, 2016; Kleinstiver et al. *Nature* 529, 490-95, 2016). A most recent single-molecule Firster resonance energy transfer (smFRET) study suggested that divalent metal ions are necessary for Cas9 conformational activation toward catalysis (Dagdas et al. *bioRxiv,* 122242, 2017). At the atomic level, however, how the metal ions aid HNH domain transition to the catalytic state remains elusive.

The knowledge of structure and dynamics of the catalytic state of HNH domain is critical for Cas9 specificity improvement. The off-target effects pose a major challenge for Cas9-mediated genome-editing applications requiring a high level of precision. Remarkably, a recent study found that CRISPR-Cas9 induced an unexpected high number of new mutations in a mouse model of gene therapy, involving thousands of single-nucleotide variants (SNVs) and hundreds of insertions and deletions (indels) (Schaefer et al. *Nat. Methods* 14, 547-548, 2017). Therefore, much effort is needed to increase the fidelity of CRISPR-Cas9 with regard to off-target mutation generation, especially in the clinical setting (Schaefer et al. *Nat. Methods* 14, 547-548, 2017). Recently, two works proposed that Cas9-guide RNA possesses more energy than needed for optimal recognition of its intended target sequence, thereby enabling cleavage at mismatched off-target sites (Slaymaker et al. *Science* 351, 84-88, 2016; Kleinstiver et al. *Nature* 529, 490-95, 2016). Based on the inactive structure of Cas9-sgRNA complex with a partial dsDNA target (Anders et al. *Nature* 513, 569-573, 2014), several high-fidelity Cas9 variants have been designed and validated for elimination of off-target effects, demonstrating the structure-guided Cas9 engineering as a robust strategy for specificity improvement (Slaymaker et al. *Science* 351, 84-88, 2016; Kleinstiver et al. *Nature* 529, 490-49, 2016). Given that all the previous efforts were based on an inactive structure, structural information of other Cas9 conformational states, especially the catalytic state, could enable further optimization of the CRISPR-Cas9 genome-editing toolbox.

SUMMARY OF THE INVENTION

The Cas9 variants of the current invention provide a solution to the off-target/fidelity problems associated with native and current Cas9 variants. In particular aspects, the amino acid variants are in the HNH domain region of Cas9. By way of example, the inventors have discovered a process to model the structure of Cas 9 in an appropriate active state, which results in the identification and design of additional variants of Cas9 having appropriate activity that enhance fidelity. Without wishing to be bound by theory, it is believed that the use of these additional variants alone or in combination with other variants results in a high fidelity Cas9 protein for use in genetic engineering methods.

Molecular dynamics (MD) is a powerful computer simulation method and has been proven to be especially useful for elucidating the structure-function relationships of biological macromolecules (Shaw et al. *Science* 330, 341-46, 2010). With two distinct MD simulation techniques, the inventors show a cross-validated catalytically active state of Cas9 HNH nuclease domain not amenable to experiments. Meanwhile, the inventors demonstrate at the atomic level the roles of $Mg^{2+}$ for formation and stability of the catalytic state. The derived catalytic model provides novel valuable structure information that can be exploited for rational engineering of high-fidelity Cas9 variants.

Generally, it has been assumed that Cas9 enhanced specificity by site-specific mutations stems from reduced binding affinities for the off-target sites. In this invention, the inventors propose that mutations designed for attenuating the activation of Cas9 HNH nuclease domain could also be employed for improving the Cas9 targeting accuracy, given the observation that HNH domain undergoes a substantial rotation of ~180 degrees during the inactive to active state transition. Thus, the Cas9 residues (except the HNH domain) forming non-specific contacts with the HNH domain or the HNH domain residues forming non-specific contacts with other Cas9 domain and/or nucleic acids (target DNA and/or gRNA) comprise the additional promising mutation sites for rational Cas9 engineering. From a physiochemical perspective, these amino acid substitutions raise the threshold energy underlying HNH conformational activation against the off-target substrates, thereby requiring more stringent Watson-Crick base pair complementarity.

Remarkably, the concept described herein expands the mutation range and mutation types for Cas9. For instance, the residues beyond the previously identified DNA-binding regions can be considered for modifications. Hence, the residues of interest are no longer limited to the polar and positively charged types. In some embodiments here, the Cas9 variants contain alterations to the acidic residues, and also, the substitutions are not limited to alanine, depending on design needs. In certain aspects the substitution can be one or more of alanine (Ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), or valine (Val, V) in place of the native amino acid.

In certain embodiments, the spCas9 variants comprise one, two, three, four or more simultaneous mutations at the following positions of SEQ ID NO:1: T13, N14, S15, S55, T58, E60, R63, R66, T67, R70, R71, Y72, R74, R78, Y136, K163, R165, H167, S217, K218, S219, E223, N235, K234, D261, K263, Q265, S267, K268, T249, N251, T270, E370, E371, E396, Q402, R403, T404, D406, N407, S409, H415, R447, Y450, Y451, R461, R494, T496, N497, K500, K510, Y515, T519, N522, K526, K528, K558, S581, E584, D585, R586, N588, T624, Y656, T657, R661, N692, Q695, H698, S730, K734, R765, N767, Q768, T769, T770, Q771, K772, Q774, K775, N776, S777, R778, E779, R780, K782, R783, N803, Q805, Q807, K810, Y812, D829, N831, R832, S834, D835, Q844, S845, K848, R859, K862, R864, K866, K890, T893, Q894, R895, D898, N899, K902, K913, K918, R919, Q920, T924, R925, Q926, T928, K929, H930, S960, K961, S964, K968, R976, H982, H983, Y1013, K1031, T1033, S1106, K1107, S1109, Y1237, Y1242, K1244, and/or K1246.

Certain embodiments are directed to modified or variant Cas9 proteins. The modified Cas9 protein comprises at least 1, 2, 3, 4, 5, 6, 7, 8, 9, 10, 11, 12, 13, 14, 15, 16, 17, 18, 19, 20, 21, 22, or 23 modifications including one or more modification or variant corresponding to Thr58, Glu60, Glu223, Glu396, Glu370, Glu371, Asp406, Glu584, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1. In certain aspects the modified Cas9 protein has at least two amino acid modifications. The modified Cas9 protein can further comprise one or more modification that includes modification of Asn14, Lys268, Glu370, Arg447, Tyr450, Asn497, Lys500, Lys526, Lys528, Lys558, Asn588, Arg661, Asn692, Gln695, Arg780, Arg783, Asn803, Gln805, Lys810, Tyr812, Asp829, Asn831, Arg832, Asp835, Gln844, Lys848, Lys862, Arg925, Gln926, Lys929, His930, Lys961, Lys968, Tyr1013, Lys1031, Lys1244, or Lys1246 corresponding to SEQ ID NO:1.

In certain embodiments the modified Cas9 protein has a modification corresponding to Thr58 of SEQ ID NO:1 in combination with one or more modification corresponding to Glu60, Glu223, Glu396, Glu370, Glu371, Asp406, Glu584, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Glu60 of SEQ ID NO:1 in combination with one or more modification corresponding to Thr58, Glu223, Glu396, Glu370, Glu371, Asp406, Glu584, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Glu223 of SEQ ID NO: 1 in combination with one or more modification corresponding to Thr58, Glu60, Glu396, Glu370, Glu371, Asp406, Glu584, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Glu396 of SEQ ID NO:1 in combination with one or more modification corresponding to Thr58, Glu60, Glu223, Glu370, Glu371, Asp406, Glu584, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Glu370 of SEQ ID NO: 1 in combination with one or more modification corresponding to Thr58, Glu60, Glu223, Glu371, Asp406, Glu396, Glu584, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Glu371 of SEQ ID NO: 1 in combination with one or more modification corresponding to Thr58, Glu60, Glu223, Glu370, Asp406, Glu396, Glu584, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Asp406 of SEQ ID NO: 1 in combination with one or more modification corresponding to Thr58, Glu60, Glu223, Glu370, Glu371, Glu396, Glu584, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Glu584 of SEQ ID NO:1 in combination with one or more modification corresponding to Thr58, Glu60, Glu223, Glu370, Asp406, Glu396, Glu371, Asp585, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Asp585 of SEQ ID NO:1 in combination with one or more modification corresponding to Thr58, Glu60, Glu223, Glu370, Asp406, Glu396, Glu371, Glu584, Arg586, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Arg586 of SEQ ID NO:1 in combination with one or more modification corresponding to Thr58, Glu60, Glu223, Glu370, Asp406, Glu396, Glu371, Glu584, Asp585, Arg765, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Arg765 of SEQ ID NO: 1 in combination with one or more modification corresponding to Thr58, Glu60, Glu223, Glu370, Asp406, Glu396, Glu371, Glu584, Asp585, Arg586, Asn767, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Asn767 of SEQ ID NO: 1 in combination with one or more modification corresponding to Thr58, Glu60, Glu223, Glu370, Asp406, Glu396, Glu371, Glu584, Asp585, Arg586, Arg765, Arg778, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Arg778 of SEQ ID NO:1 in combination with one or more modification corresponding to Thr58, Glu60, Glu223, Glu370, Asp406, Glu396, Glu371, Glu584, Asp585, Arg586, Arg765, Asn767, Glu779, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Glu779 of SEQ ID NO: 1 in combination with one or more modification corresponding to Thr58, Glu60, Glu223, Glu370, Asp406, Glu396, Glu371, Glu584, Asp585, Arg586, Arg765, Asn767, Arg778, Ser845, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Ser845 of SEQ ID NO:1 in combination with one or more modification corresponding to Thr58, Glu60, Glu223, Glu370, Asp406, Glu396, Glu371, Glu584, Asp585, Arg586, Arg765, Asn767, Arg778, Glu779, Gln844, Arg859, Arg780, Arg783, Asn803, Gln807, Tyr812, Arg864, Lys866, or Lys918 of SEQ ID NO:1.

In certain embodiments the modified Cas9 protein has a modification corresponding to Gln844 of SEQ ID NO: 1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Arg859, Arg780, Arg783, Asn803, Gln807, Tyr812, Arg864, Lys866, or Lys918 of SEQ ID NO:1.

In certain embodiments the modified Cas9 protein has a modification corresponding to Arg859 of SEQ ID NO: 1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg780, Arg783, Asn803, Gln807, Tyr812, Arg864, Lys866, or Lys918 of SEQ ID NO:1.

In certain embodiments the modified Cas9 protein has a modification corresponding to Arg780 of SEQ ID NO:1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg859, Arg783, Asn803, Gln807, Tyr812, Arg864, Lys866, or Lys918 of SEQ ID NO:1.

In certain embodiments the modified Cas9 protein has a modification corresponding to Arg783 of SEQ ID NO:1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg859, Arg780, Asn803, Gln807, Tyr812, Arg864, Lys866, or Lys918 of SEQ ID NO:1.

In certain embodiments the modified Cas9 protein has a modification corresponding to Asn803 of SEQ ID NO: 1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg859, Arg780, Arg783, Gln807, Tyr812, Arg864, Lys866, or Lys918 of SEQ ID NO:1.

In certain embodiments the modified Cas9 protein has a modification corresponding to Gln807 of SEQ ID NO: 1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg859, Arg780, Arg783, Asn803, Tyr812, Arg864, Lys866, or Lys918 of SEQ ID NO:1.

In certain embodiments the modified Cas9 protein has a modification corresponding to Tyr812 of SEQ ID NO: 1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg859, Arg780, Arg783, Asn803, Gln807, Arg864, Lys866, or Lys918 of SEQ ID NO:1.

In certain embodiments the modified Cas9 protein has a modification corresponding to Lys866 of SEQ ID NO:1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg859, Arg780, Arg783, Asn803, Gln807, Tyr812, Arg864 or Lys918 of SEQ ID NO:1.

In certain embodiments the modified Cas9 protein has a modification corresponding to Arg864 of SEQ ID NO: 1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg859, Arg780, Arg783, Asn803, Gln807, Tyr812, Lys866 or Lys918 of SEQ ID NO:1.

In certain embodiments the modified Cas9 protein has a modification corresponding to Lys918 of SEQ ID NO: 1 in combination with one or more modification corresponding to Thr58, Glu60, Glu223, Glu370, Asp406, Glu396, Glu371, Glu584, Asp585, Arg586, Arg765, Asn767, Arg778, Glu779, Ser845, Gln844, Arg859, Arg780, Arg783, Asn803, Gln807, Tyr812, Arg864 or Lys866 of SEQ ID NO: 1.

The modification can be any amino acid other than the amino acid present in a corresponding position in SEQ ID NO: 1. In a further aspect the modification can be an alanine, glycine, lysine, arginine, aspartic acid, or glutamic acid substitution. In certain aspects the modification can be of SEQ ID NO:1 in combination with one or more modification corresponding to Thr58Lys, Thr58Arg, Glu60Ala, Glu223Ala, Glu370Ala, Asp406Ala, Glu396Ala, Glu371Ala, Glu584Ala, Asp585Ala, Arg586Ala, Arg765Ala, Asn767Ala, Arg778Ala, Glu779Ala, Ser845Asp, Gln844Glu, Arg859Ala, Arg780Ala, Arg783Ala, Asn803Ala, Gln807Ala, Tyr812Ala, Lys918Ala, Arg864Ala or Lys866Ala modification corresponding to SEQ ID NO:1.

In certain embodiments, the spCas9 variants include, but not are limited to, the following combination of mutations: N588A/R765A/N767A; N588A/Q695A/R765A/N767A; N588A/N692A/R765A/N767A; N588A/N692A/R765A/R925A; N588A/N692A/N767A/R925A; N692A/R765A/N767A/R925A; Q695A/R765A/N767A/R925A; N588A/N692A/R765A/K929A; N588A/N692A/N767A/K929A; N692A/R765A/N767A/K929A; Q695A/R765A/N767A/K929A; N497A/Q695A/R765A/N767A; K526A/K528A/N497A/Q926A; K526A/K528A/K929A; K526A/R765A/N767A/Y1013A; K528A/R765A/N767A/Y1013A; K526A/R765A/N767A/Q926A; N497A/K526A/R765A/N767A; N497A/K528A/R765A/N767A; N497A/K526A/R765A/Q926A; N497A/K528A/R765A/Q926A; N588A/R765A/N767A/S845D; N588A/R765A/N767A/R832A; N588A/R765A/N767A/K862A; N588A/R765A/N767A/K866A; N588A/R765A/N767A/R859A; N588A/R765A/N767A/Q844A; N588A/R765A/N767A/K810A; N588A/R765A/N767A/K848A; N588A/R765A/N767A/E370A; N588A/R765A/N767A/E223A; N497A/N692A/K1031A/S845D; N497A/N692A/K1031A/R832A; N497A/N692A/K1031A/K862A; N497A/N692A/K1031A/K866A; N497A/N692A/K1031A/R859A; N497A/N692A/K1031A/Q844A; N497A/N692A/K1031A/K810A; N497A/N692A/K1031A/K848A; N497A/N692A/K1031A/E370A; N497A/N692A/K1031A/E223A; N497A/N695A/K1031A/S845D; N497A/N695A/K1031A/R832A; N497A/N695A/K1031A/K862A; N497A/N695A/K1031A/K866A; N497A/N695A/K1031A/R859A; N497A/N695A/K1031A/Q844A; N497A/N695A/K1031A/K810A; N497A/N695A/K1031A/K848A; N497A/N695A/K1031A/E370A; N497A/N695A/K1031A/E223A; K526A/N695A/K1031A/S845D; K526A/N695A/K1031A/R832A; K526A/N695A/K1031A/K862A; K526A/N695A/K1031A/K866A; K526A/N695A/K1031A/R859A; K526A/N695A/K1031A/Q844A; K526A/N695A/K1031A/K810A; K526A/N695A/K1031A/K848A; K526A/N695A/K1031A/E370A; K526A/N695A/K1031A/E223A; K528A/N695A/K1031A/S845D; K528A/N695A/K1031A/R832A; K528A/N695A/K1031A/K862A; K528A/N695A/K1031A/K866A; K528A/N695A/K1031A/R859A; K528A/N695A/K1031A/Q844A; K528A/N695A/K1031A/K810A; K528A/N695A/K1031A/K848A; K528A/N695A/K1031A/E370A; K528A/N695A/K1031A/E223A; N692A/R765A/Y1013A; N692A/R765A/S845D/Y1013A; N692A/R765A/R832A/Y1013A; N692A/R765A/K862A/Y1013A; N692A/R765A/K866A/Y1013A; N692A/R765A/R859A/Y1013A; N692A/R765A/Q844A/Y1013A; N692A/R765A/K810A/Y1013A; N692A/R765A/K848A/Y1013A; N692A/R765A/E370A/Y1013A; N692A/R765A/E223A/Y1013A; N692A/R765A/Y1013A; N692A/Q695A/K810A/Y1013A; N692A/Q695A/K848A/Y1013A; K526A/K528A/Y1013A; K526A/K528A/K268A/Y1013A; R447A/K526A/K528A/Y1013A; R765A/K929A/H930A; R765A/K929A/S845D/Y1013A; R765A/K929A/R832A/Y1013A; R765A/K929A/K862A/Y1013A; R765A/K929A/K866A/Y1013A; R765A/K929A/R859A/Y1013A; R765A/K929A/Q844A/Y1013A; R765A/K929A/K810A/Y1013A; R765A/K929A/K848A/Y1013A; R765A/K929A/E370A/Y1013A; R765A/K929A/E223A/Y1013A; R765A/Q926A/K929A/H930A; R447A/K500A/R661A; K500A/N695A/K929A/S845D; K500A/N695A/K929A/R832A; K500A/N695A/K929A/K862A; K500A/N695A/K929A/K866A; K500A/N695A/K929A/R859A; K500A/N695A/K929A/Q844A; K500A/N695A/K929A/K810A; K500A/N695A/K929A/K848A; K500A/N695A/K929A/E370A; K500A/N695A/K929A/E223A; R765A/R925/Q926A; R765A/R925/Q926/Y1013A; N14A/K961A/K968A; N14A/K961A/K968A/S845D; N14A/K961A/K968A/K848A; R447A/R765A/Y1013A; K526A/N588A/R765A/N767A; N588A/K929A/H930A/Y1013A; R447A/K526A/K929A; N588A/N767A/Y1013A/K866A; N588A/N767A/Y1013A/S845D; K268A/K526A/N588A/N767A; N14A/K526A/K866A/K1246A; N14A/R447A/Y1013A/K1246A; N588A/R765A/D835A/K1246A; N14A/R447A/R765A/S845D; K1244A/K1246A/K848A; K1244A/K1246A/K810A; K1244A/K1246A/R832A; K1244A/K1246A/K862A; K1244A/K1246A/K866A; K1244A/K1246A/R859A; K1244A/K1246A/E370A; K1244A/K1246A/E223A; K1244A/K1246A/S845D; K1244A/K1246A/Q844A; K1244A/K1246A/Q844A/K1031A; K1244A/K1246A/Q844A/Y1013A; K1244A/K1246A/Q844A/N695A; K1244A/K1246A/Q844A/N692A; K1244A/K1246A/Q844A/N588A; K1244A/K1246A/Q844A/N767A; K1244A/K1246A/Q844A/Q926A; K268A/R447A/Y450A/K1031A; K268A/R447A/Y450A/Y1013A; K268A/R447A/Y450A/N695A; K268A/R447A/Y450A/N692A; K268A/R447A/Y450A/N588A; K268A/R447A/Y450A/N767A; K268A/R447A/Y450A/Q926A; N14A/K268A/R447A/Y450A; N14A/Y450A/K526A/K528A; N14A/Y450A/R765A/S845D; N14A/Y450A/R765A/R832A; N14A/Y450A/R765A/K862A; N14A/Y450A/R765A/K866A; N14A/Y450A/R765A/R859A; N14A/Y450A/R765A/Q844A; N14A/Y450A/R765A/K810A; N14A/Y450A/R765A/K848A; N14A/Y450A/R765A/E370A; N14A/Y450A/R765A/E223A; R447A/Y450A/R765A/S845D; R447A/Y450A/R765A/R832A; R447A/Y450A/R765A/K862A; R447A/Y450A/R765A/K866A; R447A/Y450A/R765A/R859A; R447A/Y450A/R765A/Q844A; R447A/Y450A/R765A/K810A; R447A/Y450A/R765A/K848A; R447A/Y450A/R765A/E370A; R447A/Y450A/R765A/E223A; K268A/R447A/R765A/S845D; K268A/R447A/R765A/R832A; K268A/R447A/R765A/K862A; K268A/R447A/R765A/K866A; K268A/R447A/R765A/R859A; K268A/R447A/R765A/Q844A; K268A/R447A/R765A/K848A; K268A/R447A/R765A/K810A; K268A/R447A/R765A/E370A; K268A/R447A/R765A/E223A; Q805A/D829A/N831A/D835A; R765A/D829A/D835A/Y1013A; R918A/D829A/D835A/Y1013A; R895A/D829A/D835A/Y1013A; K500A/D829A/D835A/Y1013A; K929A/D829A/

D835A/Y1013A; R780A/D829A/D835A/Y1013A; R783A/ D829A/D835A/Y1013A; R765A/D829A/D835A/N695A; R918A/D829A/D835A/N695A; R895A/D829A/D835A/ N695A; K500A/D829A/D835A/N695A; K929A/D829A/ D835A/N695A; R780A/D829A/D835A/N695A; R783A/ D829A/D835A/N695A; N695A/R780A/R783A/S845D; N695A/R780A/R783A/R832A; N695A/R780A/R783A/ K862A; N695A/R780A/R783A/K866A; N695A/R780A/ R783A/R859A; N695A/R780A/R783A/Q844A; N695A/ R780A/R783A/K810A; N695A/R780A/R783A/K848A; N695A/R780A/R783A/E370A; N695A/R780A/R783A/ E223A; N692A/R780A/R783A/S845D; N692A/R780A/ R783A/R832A; N692A/R780A/R783A/K862A; N692A/ R780A/R783A/K866A; N692A/R780A/R783A/R859A; N692A/R780A/R783A/Q844A; N692A/R780A/R783A/ K810A; N692A/R780A/R783A/K848A; N692A/R780A/ R783A/E370A; N692A/R780A/R783A/E223A; N692A/ R780A/N803A/S845D; N692A/R780A/N803A/R832A; N692A/R780A/N803A/K862A; N692A/R780A/N803A/ K866A, N692A/R780A/N803A/R859A; N692A/R780A/ N803A/Q844A; N692A/R780A/N803A/K810A; N692A/ R780A/N803A/K848A; N692A/R780A/N803A/E370A; N692A/R780A/N803A/E223A; N692A/R783A/N803A/ S845D; N692A/R783A/N803A/R832A; N692A/R783A/ N803A/K862A; N692A/R783A/N803A/K866A; N692A/ R783A/N803A/R859A; N692A/R783A/N803A/Q844A; N692A/R783A/N803A/K810A; N692A/R783A/N803A/ K848A; N692A/R783A/N803A/E370A; N692A/R783A/ N803A/E223A; N695A/R783A/N803A/S845D; N695A/ R783A/N803A/R832A; N695A/R783A/N803A/K862A; N695A/R783A/N803A/K866A; N695A/R783A/N803A/ R859A; N695A/R783A/N803A/Q844A; N695A/R783A/ N803A/K810A; N695A/R783A/N803A/K848A; N695A/ R783A/N803A/E370A; N695A/R783A/N803A/E223A; N695A/R783A/Y812A/S845D; N695A/R783A/Y812A/ R832A; N695A/R783A/Y812A/K862A; N695A/R783A/ Y812A/K866A; N695A/R783A/Y812A/R859A; N695A/ R783A/Y812A/Q844A; N695A/R783A/Y812A/K810A; N695A/R783A/Y812A/K848A; N695A/R783A/Y812A/ E370A; N695A/R783A/Y812A/E223A; K500A/N588A/ S845D/Y1013A; K500A/N588A/R832A/Y1013A; K500A/ N588A/K862A/Y1013A; K500A/N588A/K866A/Y1013A; K500A/N588A/R859A/Y1013A; K500A/N588A/Q844A/ Y1013A; K500A/N588A/K810A/Y1013A; K500A/N588A/ K848A/Y1013A; K500A/N588A/E370A/Y1013A; K500A/ N588A/E223A/Y1013A; K500A/N588A/S845D/Y1013A; N588A/N692A/K1244A/K1246A; R447A/R765A/N497A; R447A/R765A/K929A; R447A/R765A/N767A; R447A/ R765A/N767A/K558A; R447A/R765A/N767A/R586A; R447A/R765A/N767A/K1244A; R447A/R765A/N767A/ K1246A; R447A/R765A/N767A; R447A/N695A/R765A/ N767A; R447A/R765A/N695A/K558A; R447A/R765A/ N695A/R586A; R447A/R765A/N695A/K1244A; R447A/ R765A/N695A/K1246A; R447A/R765A/N767A/K1246A; R447A/N695A/R765A/N767A; R447A/R765A/N695A/ K558A; R447A/R765A/N695A/R586A; R447A/R765A/ N695A/K1244A; R447A/R765A/N695A/K1246A; R447A/ N692A/R765A/N767A; R447A/R765A/N692/K558A; R447A/R765A/N692/R586A; R447A/R765A/N692/ K1244A; or R447A/R765A/N692/K1246A.

Certain embodiments are directed to modified Cas9 protein having the Cas9 modification selected from K526A/ N588A/R765A/N767A; N588A/K929A/H930A/Y1013A; R447A/K526A/K929A; N588A/N767A/Y1013A/K866A; N588A/N767A/Y1013A/S845D; K268A/K526A/N588A/ N767A; N14A/K526A/K866A/K1246A; N14A/R447A/ Y1013A/K1246A; N588A/R765A/D835A/K1246A; or N14A/R447A/R765A/S845D. In particular aspects the Cas9 modification is N588A/R765A/D835A/K1246A or N14A/ R447A/R765A/S845D.

The modified Cas9 protein can be coupled or fused with a heterologous polypeptide or peptide. In certain aspects the modified Cas9 protein can include a nuclear localization signal, a cell penetrating amino acid sequence, or an affinity tag.

In certain aspects the modified Cas9 protein is a modified *Streptococcus pyogenes* Cas9 protein. In a further aspect the modified Cas9 protein can be 70, 75, 80, 85, 90, 95, 96, 97, 98, 99% identical to SEQ ID NO: 1, while retaining at least some of the Cas9 function of the protein of SEQ ID NO:1. The modified Cas9 protein can have at least 20, 30, 40, 50, 60, 70, 80, 90% fewer off-target events as compared to non-modified Cas9. Furthermore, the modified Cas9 protein can cleave at least 60, 65, 70, 75, 80, 85, 90, 95, to 100%, including all values and ranges there between, of the target sites as compared to non-modified Cas9, thus maintaining sufficient activity. The modified Cas9 protein can have a frequency of off-site events that is at least 20, 30, 40, 50, 60, 70, 80, 90% lower than off-target events as compared to non-modified Cas9. Specificity (fidelity) and cleavage activity of Cas9 variant are quantified as compared with the wild type protein. A gRNA targets a specific gene sequence, therefore there are a certain number of known off-target sequences. The native Cas9/gRNA complex is able to cleave the target DNA and all the off-target DNA sequences. The modified Cas9 protein reduces the cleavage of the off-target DNA sequence. The specificity (fidelity) can be determined by measuring the number of off-target cleavage. The lower number of off-target site cleavages, the higher the specificity (fidelity). For example, if a designed Cas9 mutant yields cleavage only at 10% of the off-target sites compared to the wild type protein, meaning 90% fewer off-target events, the gene editing specificity can be regarded as improving by 90%. The on-target activities of Cas9 proteins can be assessed using the human cell-based enhanced GFP (EGFP) disruption assay. For example, the wild type Cas9 guided by a fully matched gRNA induces 90% EGFP disruption, a certain Cas9 variant exhibiting a disruption percentage around that value (80%, 95%, for example) is considered as possessing the wild-type or near wild-type cleavage efficiency. In certain aspects of the invention, the criterion of >70% of wild-type activity is used for screening potential Cas9 variants for subsequent tests on a whole-genome level.

Certain embodiments are directed to a fusion protein comprising the modified Cas9 protein fused to a heterologous peptide or protein, with an optional intervening linker.

Other embodiments are directed to an expression cassette encoding the modified Cas9 protein or fusion protein comprising the modified Cas9 protein.

Still other embodiments are directed to an expression vector comprising the expression cassette encoding the modified Cas9 protein or fusion protein comprising the modified Cas9 protein.

Certain embodiments are directed to a host cell expressing an expression cassette of the invention. In certain aspects the host cell is an isolated host cell or a host in culture.

Other embodiments are directed to a host cell comprising a modified Cas9 protein described herein.

Certain embodiments are directed to methods of using such a modified Cas9 protein. Certain aspects include methods of altering the genome of a cell, the method comprising expressing in the cell or contacting the cell with the modified Cas9 protein described herein. In a further aspect the modified Cas9 protein is linked to a guide RNA having a region complementary to a selected portion of the genome of the cell. The method resulting in the alteration of the genome of the cell.

Other embodiments are directed to an active state model of the HNH domain of Cas9 comprising a divalent cation at the interface of a ββα motif and a scissile phosphate. In certain aspects the divalent cation is Mg, Mn, Ca, or Co.

Still other embodiments are directed to methods of modeling an active state of a Cas9 HNH domain. The methods can comprise at least the steps of (a) aligning a scissile phosphate and flanking nucleotides of a T4 Endo VII system (2QNC) to corresponding tDNA stretch in the Cas9 complex of the pre-catalytic state (5F9R); (b) calculating a tDNA transformation matrix from the paired ββα motifs in the two nucleases, resulting in a model of the HNH domain docked at the cleavage site; (c) repeating a and b, replacing the crystal structure (5F9R) with snapshot structures from the sets of long cMD trajectories; (d) replacing the α segment of the ββα-Me motif in the optimized Cas9 complex from c with the corresponding part in the Mg2+-bound apo-Cas9 structure (4CMP); (e) performing long cMD simulations to obtain active state of Cas9.

Other embodiments are directed to methods of altering a double stranded DNA (dsDNA) molecule, the method comprising contacting the dsDNA molecule with the modified Cas9 protein described herein. The modified Cas9 protein can be linked to a guide RNA having a region complementary to a selected portion of the dsDNA molecule, resulting in the alteration of the dsDNA molecule.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa.

The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, homologs, orthologs, paralogs, fragments and other equivalents, variants, and analogs of the foregoing.

The term "variant" or "mutant" refers to an amino acid sequence that is different from the reference polypeptide by one or more amino acids, e.g., one or more amino acid substitutions. For example a modified or variant Cas9 polypeptide differs from wild-type Cas9 (e.g., SEQ ID NO:1) by one or more amino acid substitutions, i.e., mutations.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, double-stranded, or a mixture of single- and double-stranded regions.

"Substantially similar" with respect to nucleic acid or amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity. Such identity can be determined using algorithms known in the art, such as the mBLAST algorithm.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a cell or a subject; in other words, the polypeptide may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

The term "providing" is used according to its ordinary meaning "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, and/or peptides.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods of making and using the same of the present invention can "comprise," "consist essentially of," or "consist of" particular ingredients, components, blends, method steps, etc., disclosed throughout the specification.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION OF THE INVENTION

The bacterial CRISPR-Cas9 system has been adapted as a powerful and versatile genome-editing toolbox. The system holds immense promise for future therapeutic applications. Despite recent advances in Cas9 structure/function, little is known on the catalytic state of Cas9 HNH nuclease domain and it remains elusive how the divalent metal ions affect the HNH domain conformational transition. A deep understanding of Cas9 activation and cleavage mechanism can enable further optimization of Cas9-based genome-editing specificity and efficiency. Using two distinct molecular dynamics simulation techniques, the inventors obtained a cross-validated catalytically active state of Cas9 HNH domain primed for cutting the target DNA strand. Moreover, the inventors demonstrate at the atomic level the essential roles of the catalytic $Mg^{2+}$ for the active state formation and stability. Furthermore, the inventors show that the derived catalytic conformation of HNH domain can be exploited for rational engineering of Cas9 variants with enhanced specificity.

Figures 5A, 5B, 5C, 5D, 5E, 5F:
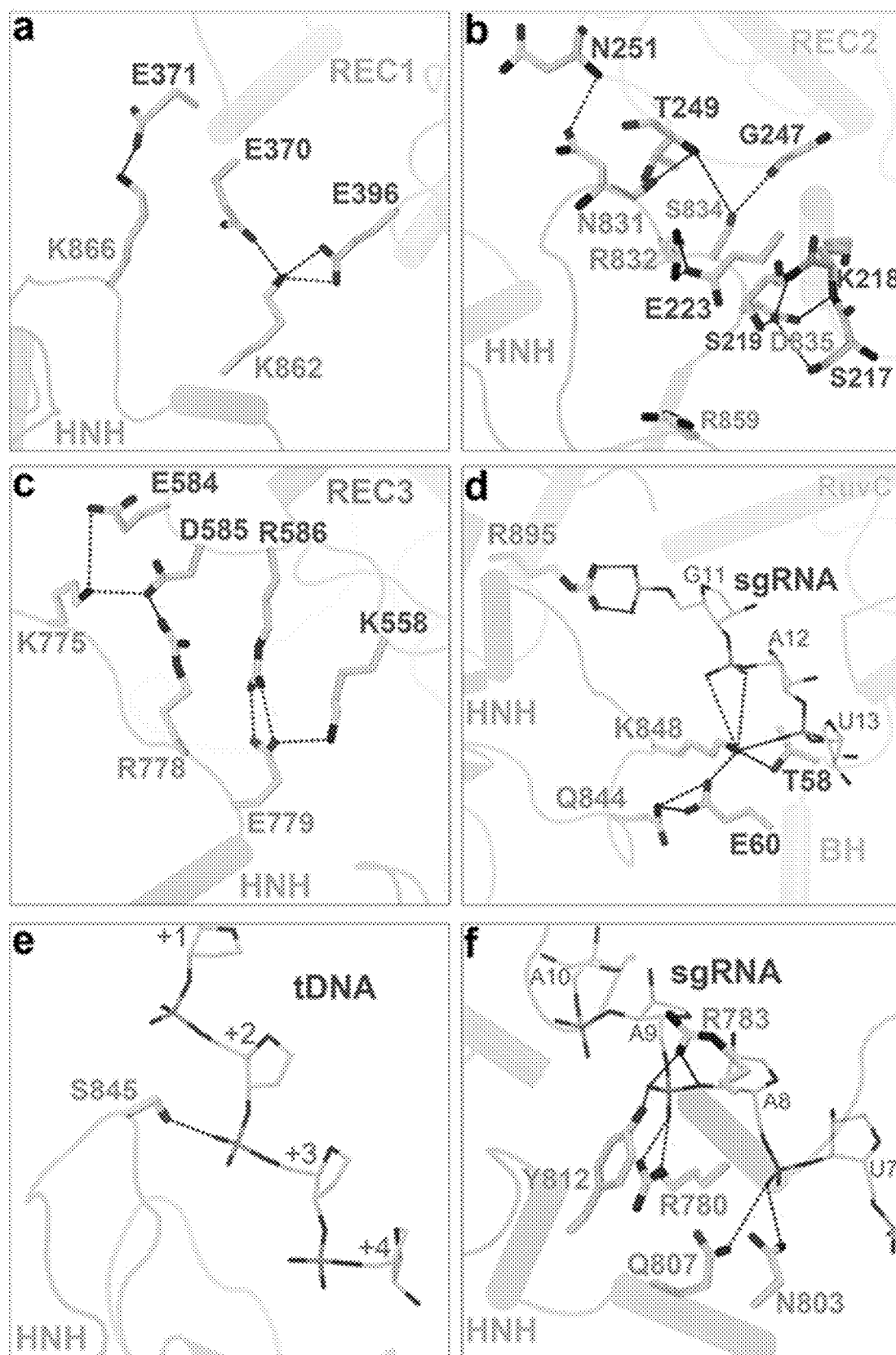
FIGS. 5a-5f. New interactions established between the catalytic HNH domain and other components in the complex system identified from the post target-MD (tMD) simulations. (a) Interactions with the REC1 domain. (b) Interactions with the REC2 domain. (c) Interactions with the REC3 domain. (d) Interactions with the bridge helix (BH) and sgRNA. (e) Interactions with the tDNA. (f) Interactions with the sgRNA. The HNH domain residues are highlighted. The dash lines denote the salt bridges and/or hydrogen bonds. Due to space limit, only interacting pairs with relatively high occupancy throughout the simulations are shown here, and the complete residue list is present in Table 4. This figure is comparable to FIG. 14.
Figure 6:
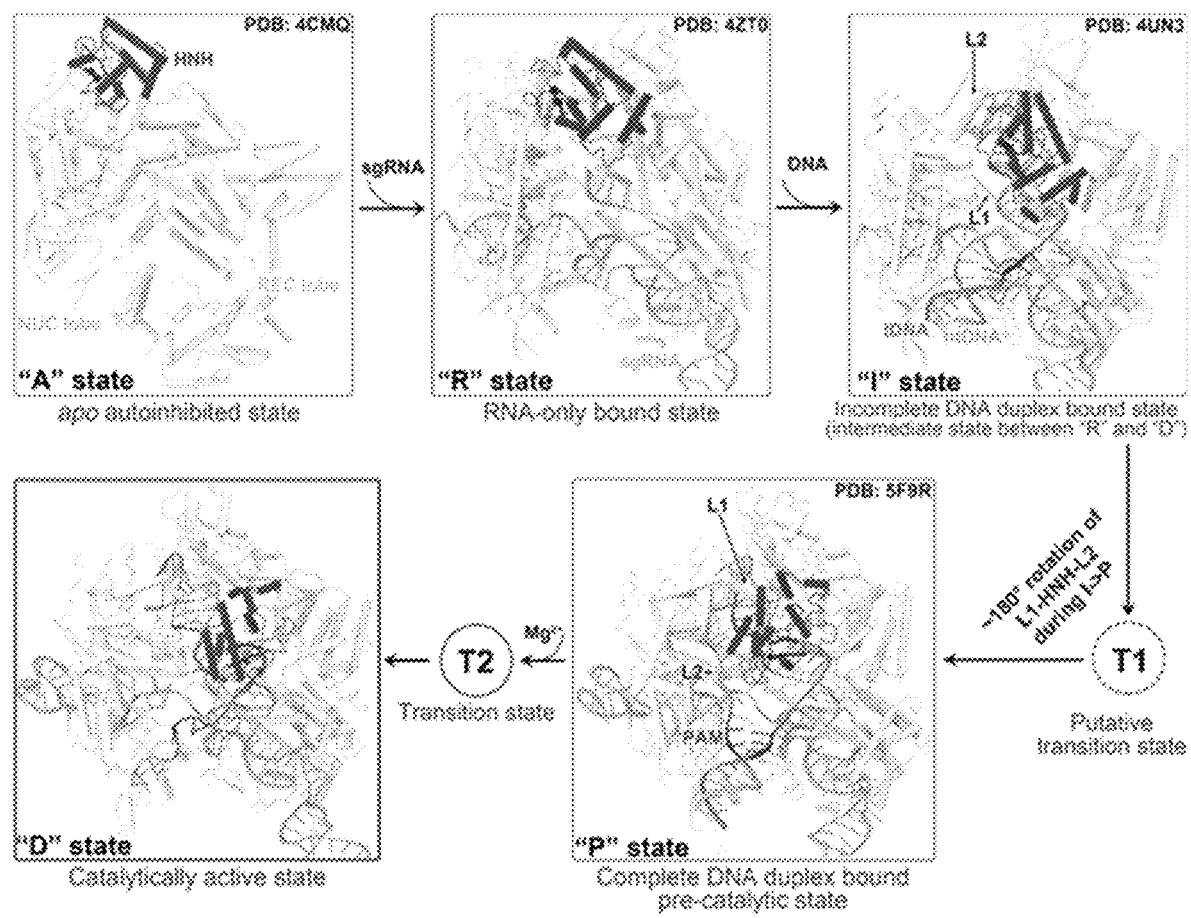
FIG. 6. Conformational activation pathway of Cas9 HNH nuclease domain. The HNH domain and flanking liker regions (i.e., L1 and L2) are highlighted. The PAM and the three putative catalytic residues of HNH domain are represented as blue spheres. The dash lines denote the disordered liker loops. All of the solved Cas9 crystal structures in different binding forms assume an inactive state as for both RuvC and HNH nuclease domains. Using single-molecule FRET, Dagdas et al. (Dagdas et al., bioRxiv, 122242, 2017) identified three distinct conformational states of Cas9, designated state "R", "I" and "D", respectively. In the inventors study, with the involvement of Mg$^{2+}$ and absence of ntDNA, they addressed how the HNH domain is "docked" toward the catalytically competent state. However, another fundamental question remains open to be answered that what factors trigger ~180° rigid-body rotation of HNH domain alongside its two flanking likers during I→P state transition. The inventors propose that there likely exists a functionally important transition state (Ti) between I and P states that acts a conformational checkpoint determining the fates (cleaved or not) of bound on- or off-target substrates.
Figures 8A, 8B, 8C, 8D, 8E, 8F:
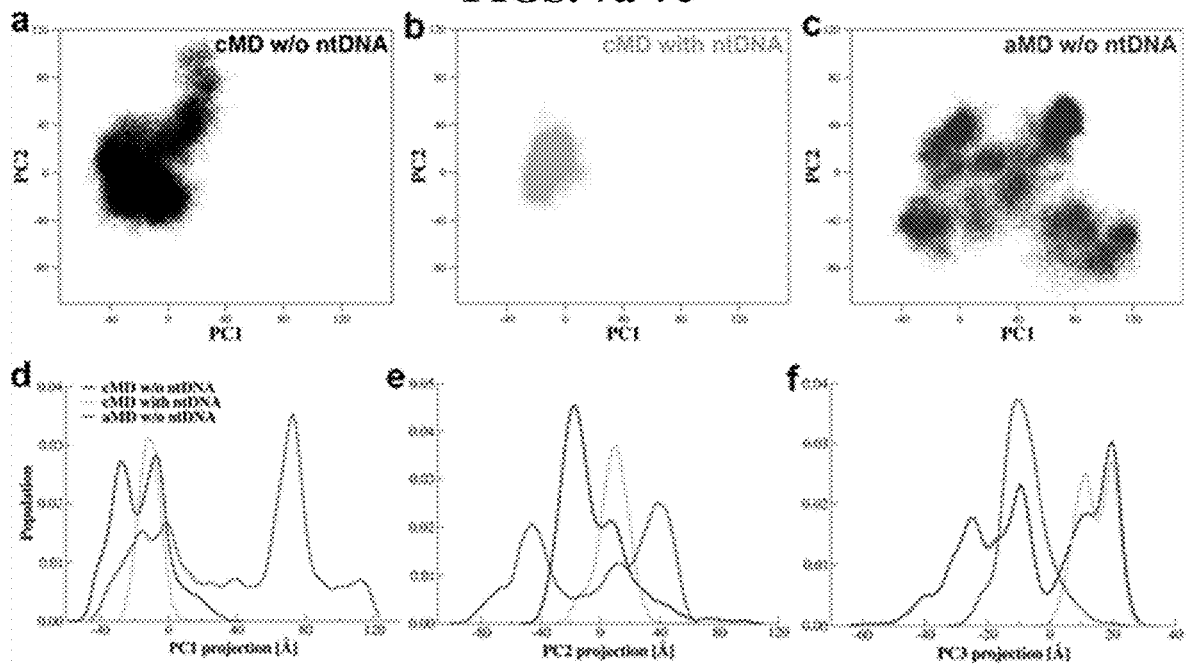
FIGS. 8a-8f. Molecular Dynamic (MD) simulations. (a-c) Projections of the conventional MD simulations without ntDNA (cMD w/o ntDNA) (a), conventional MD simulations with ntDNA (cMD with ntDNA) (b) and accelerated MD simulations without ntDNA (aMD w/o ntDNA) (c) onto the first two eigen-vectors calculated from the whole trajectories for the HNH domain. (d-f) overlap of the histograms of the first (d), second (e) and third (f) PC projections for the conventional MD simulations without ntDNA (cMD w/o ntDNA, black line), conventional MD simulations with ntDNA (cMD with ntDNA, green line) and accelerated MD simulations without ntDNA (aMD w/o ntDNA, red line) and. See also FIG. 1.
Figures 9A, 9B:
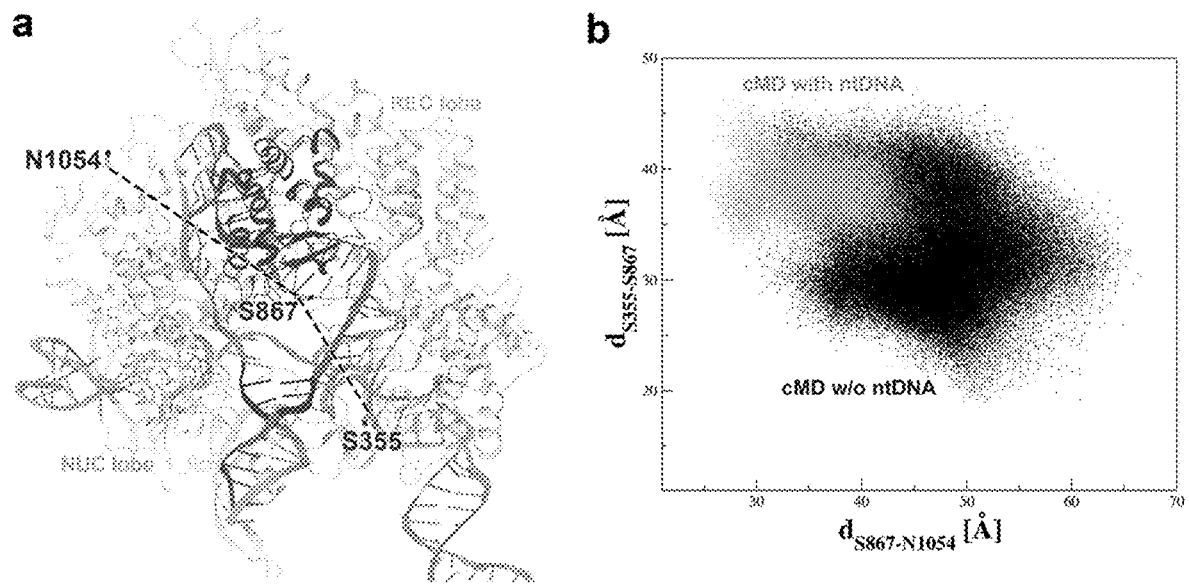
FIGS. 9a-9b. (a) FRET labeled residue pairs shown with 5F9R and (b) scatter plot of the distances for the labeled residue pairs calculated from conventional MD simulations without ntDNA (cMD w/o ntDNA, black dots) and with ntDNA (cMD with ntDNA, green dots). Ser355, Ser867 and Asn1054 are located in the REC1, HNH and RuvC domains, respectively. These residues were previously selected to characterize different conformational states of HNH domain in FRET experiments (Dagdas et al., bioRxiv, 122242, 2017).

The Cas9 crystal structures in different binding forms have been solved over the past few years (Jiang et al. *Science* 351, 867-871, 2016; Jiang et al. *Science* 348, 1477-1481, 2015; Nishimasu et al. *Cell* 156, 935-949, 2014; Anders et al. *Nature* 513, 569-573, 2014; Jinek et al. *Science* 343, 1247997, 2014), however, none of them assumes a functionally fully active state as for either of its two nuclease domains (FIG. 6). In recent work, the inventors reported the catalytically competent state of Cas9 RuvC domain primed for cutting the ntDNA by molecular dynamics (MD) simulations (Zuo and Liu, *Sci. Rep.* 5, 2016). Using two distinct sampling strategies, i.e., the biased tMD and unbiased cMDens, well-converged catalytic conformations for the HNH domain were obtained, especially in terms of HNH domain orientation (FIG. 1 and FIG. 4), $Mg^{2+}$ coordination geometry (FIG. 2) and newly established interactions with HNH domain (FIG. 5 and FIG. 14). The success of cMD$^{ens}$ here can be ascribed to: (i) enhanced flexibility of HNH domain by removal of ntDNA (FIG. 1 and FIG. 8-9); (ii) $Mg^{2+}$-mediated electrostatic attraction at the binding interface (FIG. 2 and FIG. 4); and (iii) favorable charged and polar interactions between HNH domain and other components (FIG. 5 and FIG. 14). Apparently, these factors largely lower the energetic barrier between the pre-catalytic and catalytic states, thereby making it possible that a large conformational change of HNH domain (FIG. 3 and FIG. 13 and Table 3) could be accessible within dozens of microseconds (Table 1). The cMD$^{ens}$-based sampling approach might be applied to other systems provided the conformational transition pathway can be defined.

In order to enhance the conformational dynamics of HNH domain, the ntDNA was not included in the inventors simulations. The inventors contemplate that the ntDNA might stabilize the catalytic conformation by interactions with the linker 2 (L2) region flanking C-terminus of the HNH domain (Jiang et al. *Science* 351, 867-871, 2016; Zuo and Liu, *Sci. Rep.* 5, 2016; Palermo et al. *ACS Cent. Sci.*, 2016). Noticeably, cleavage assays suggest that a single-stranded tDNA substrate was cleaved two orders of magnitudes slower than a dsDNA substrate, despite comparable binding affinities of both substrates to Cas9-gRNA (Sternberg et al. *Nature* 507, 62-67, 2014). Concerning the cleavage of tDNA in the duplex context, the inventors reason that the ntDNA accelerates the reaction rates probably by promoting the HNH domain rotation during strand unwinding (FIG. 6) and/or by facilitating rapid interrogation and loading of the DNA target via PAM recognition (Sternberg et al. *Nature* 507, 62-67, 2014). In the presence of ntDNA, the Cas9 catalytic state might adopt a somewhat different conformation from that captured here. Yet the global orientation of HNH domain relative to the REC lobe and tDNA, and the coordination configuration at the binding interface should vary little. The inventors have bridged the missing link of how the HNH domain transitions from the pre-catalytic to catalytic state. However, another fundamental question remains open to be answered that what factors trigger ~180° rigid-body rotation of L1-HNH-L2 during the previously identified immediate ("I") to pre-catalytic ("P") state transition (FIG. 6). The inventor contemplate that there likely exists a functionally relevant transition state between the I and P states, which acts a conformational checkpoint determining the fates (cleaved or not) of bound on- or off-target substrates. By introducing a certain number of mismatches, this state might be captured through smFRET or crystallography, or identified with molecular dynamics free energy simulations (Giulia et al. *Proc. Natl. Acad. Sci. U.S.A.* 2017).

The two distinct conformational activation pathways for the HNH domain, implemented respectively by tMD and cMDens, strongly suggest $Mg^{2+}$ is indispensable for the catalytic state formation and stability. In the absence of $Mg^{2+}$, it is conceivable that the HNH domain swings repeatedly toward and away from the tDNA but fails to visit an active conformation (FIG. 4), as demonstrated by the smFRET experiments (Dagdas et al. *bioRxiv*, 122242, 2017). If $Mg^{2+}$ diffuses into the binding interface, the HNH domain readily docks onto and gets stable association with the opposite tDNA, accompanying new interactions formed with other components (especially REC lobe and sgRNA) in the system. Therefore, beyond its catalytic role, $Mg^{2+}$ also acts as a facilitator and stabilizer of the functional conformational state. Combining with the inventors previous study with Cas9 RuvC domain (Zuo and Liu, *Sci. Rep.* 5, 2016), more generally, the inventors hold that the roles of $Mg^{2+}$ revealed here are common in other divalent metal ion dependent nucleases (Yang, *Q. Rev. Biophys.* 44, 1-93, 2011; Yang et al. *Mol. Cell* 22, 5-13, 2006). Besides $Mg^{2+}$, other metal ions like $Mn^{2+}$, $Ca^{2+}$ and $Co^{2+}$ are also able to activate HNH conformation and stabilize its catalytic state (Zuo and Liu, *Sci. Rep.* 5, 2016; Dagdas et al. *bioRxiv*, 122242, 2017), which might be explained by the fact that these ions can assume a similar octahedral ordination geometry and a comparable effective radius to that of $Mg^{2+}$ as observed here (FIG. 2)(Shannon, *Acta crystallographica section A: crystal physics, diffraction, theoretical and general crystallography* 32, 751-767, 1976). Intriguingly, $Co^{2+}$ does not support HNH nuclease activity (Zuo and Liu, *Sci. Rep.* 5, 2016; Dagdas et al. *bioRxiv*, 122242, 2017). Hence the catalytic conformation might be crystalized with wild-type Cas9 and $Co^{2+}$. This strategy could be more effective than using Cas9 nickase mutants and $Mg^{2+}$, as the active residue substitution inevitably destabilizes the enzyme/substrate complex.

Figures 14A, 14B, 14C, 14D, 14E, 14F:
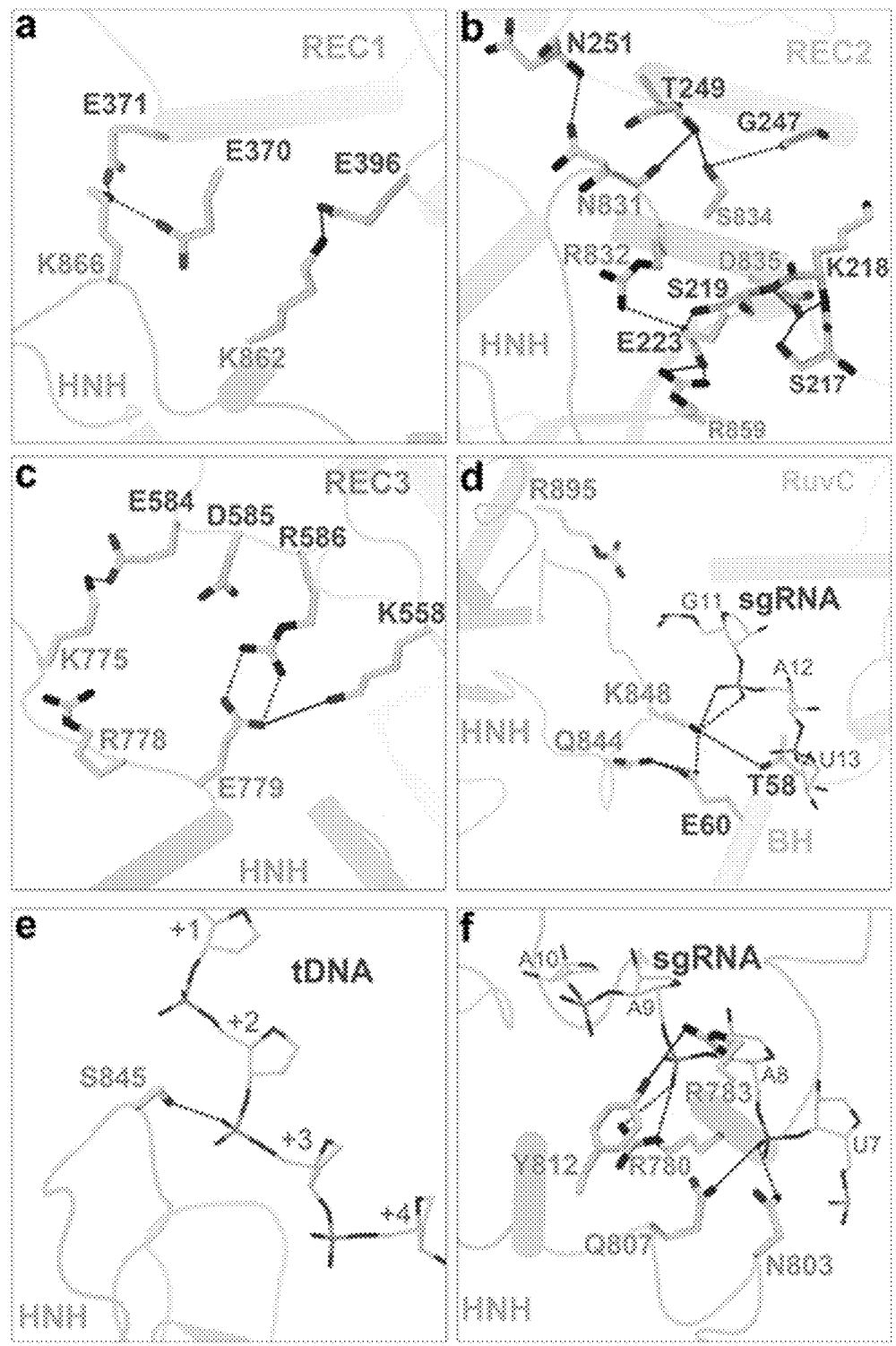
FIG. 14a-14f. New interactions established between the catalytic HNH domain and other components in the complex system identified from the conventional ensemble MD (cMDens) simulations. (a) Interactions with the REC1 domain. (b) Interactions with the REC2 domain. (c) Interactions with the REC3 domain. (d) Interactions with the bridge helix (BH) and sgRNA. (e) Interactions with the tDNA. (f) Interactions with the sgRNA. The HNH domain residues are highlighted. The dash lines denote the salt bridges and/or hydrogen bonds. Note that all the interacting pairs do not necessarily appear in one single snapshot, and the complete residue list is present in Table 4. This figure is comparable to FIG. 5.

The derived catalytic state provides a different perspective on the sources of enhanced Cas9 specificity through alanine mutagenesis. The four basic residues of L1 linker and HNH domain, Lys775, Arg832, Lys862 and Lys848, whose single alanine substitution was shown to reduce Cas9 off-target effects (FIG. 7c), were previously supposed to make contacts with the phosphate backbone of ntDNA (Slaymaker et al. *Science* 351, 84-88, 2016). From simulations, Lys775, Arg832 and Lys862 form ionic/hydrogen-bonding interactions with the negatively charged residues on the REC3 (Glu584 and Asp585), REC2 (Glu223) and REC1 (Glu370 and Glu396) domain, respectively, while another residue Lys848 is simultaneously engaged to the residues on BH (Thr68 and Glu60) and sgRNA backbone (FIG. 5, FIG. 14 and Table 4). Apparently, these new interactions directly contribute to HNH domain docking onto tDNA, and neutralization of the basic residues could destabilize formation of the active HNH conformation, thereby entailing more stringent Watson-Crick base pair complementarity with sgRNA. This view is in contrast with the hypothesis that the improved specificity exclusively results from diminished interactions with the ntDNA (Slaymaker et al. *Science* 351, 84-88, 2016). Remarkably, the catalytic model described herein accounts for why the identified Cas9 (K848A/ K1003A/R1060) variant [referred to as eSpCas9(1.1) in Slaymaker et al. *Science* 351, 84-88, 2016] exhibits genome-wide high editing specificity, which is rooted in a combined effect involving simultaneous weakened binding with the two DNA strands, sgRNA and Cas9 BH. Meanwhile, the inventors highlight that it cannot be ruled out that the basic residues of HNH domain change interacting partners (e.g. from ntDNA to tDNA) during different stages of conformational activation, given the striking flexibility of HNH domain (see FIG. 6). Moreover, our model could also explain the decrease in specificity upon converse Ser845Lys replacement (Slaymaker et al. *Science* 351, 84-88, 2016), which arises from strengthened interaction of HNH domain with the tDNA backbone at a position only 1-bp from the cleavage site (FIG. 5e and FIG. 14e).

In the framework of the "excess energy" hypothesis proposed for Cas9-sgRNA (Slaymaker et al. *Science* 351, 84-88, 2016; Kleinstiver et al. *Nature* 529, 490-495, 2016), likewise, the new structural information here can be exploited to rationally design more Cas9 variants with improved specificity. After careful inspection of the locations of the identified residues and their interactions within the whole complex, the inventors suggest more than a dozen sites to be mutated (See Table 4). Further integration with previously screened candidate sites, it is believed that different versions of high-fidelity Cas9 mutants could be customized specially for minimizing the off-target effects occurring at the PAM proximal or distal ends, or even at the non-standard repetitive sites. It would make more sense, as there is no one versatile Cas9 nuclease capable of eliminating all sorts of off-target cleavage.

In summary, a cross-validated catalytically active model of Cas9 HNH nuclease domain poised for cutting the tDNA was discovered and demonstrate the essential roles of divalent metal ions in facilitating and stabilizing the active conformation formation. More importantly, the derived catalytic state provides novel structure information for Cas9 specificity enhancement. Further studies on more different conformational states as well as the binding and cleavage mechanism of Cas9 would contribute to additional refinement of the CRISPR-Cas9 genome-editing toolbox.

Activities of modified Cas9 polypetpides can be assessed in a bacterial cell-based system with survival percentages between 50-100% usually indicating robust cleavage, whereas 0% survival indicated that the enzyme had been functionally compromised.

To further determine whether the Cas9 variants described herein function efficiently in human cells, modified proteins can be tested using a human cell-based EGFP-disruption assays. In this assay, successful cleavage of a target site in the coding sequence of a single integrated, constitutively expressed EGFP gene leds to the induction of mutations and disruption of EGFP activity, which can be quantitatively assessed by flow cytometry (see, for example, Reyon et al., *Nat Biotechnol.* 30(5):460-5, 2012).

All of the Variants Described Herein can be Incorporated into Existing Vectors

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria or other host cell expression system.

The term "functionally equivalent codon" is used herein to refer to codons that encode the same amino acid, such as the six codons for arginine or serine, and also refers to codons that encode biologically equivalent amino acids. Codons include: Alanine (Ala, A) GCA, GCC, GCG, and GCU; Cysteine (Cys, C) UGC and UGU; Aspartic acid (Asp, D) GAC and GAU; Glutamic acid (Glu, E) GAA and GAG; Phenylalanine (Phe, F) UUC and UUU; Glycine (Gly, G) GGA, GGC, GGG, and GGU; Histidine (His, H) CAC and CAU; Isoleucine (Ile, I) AUA, AUC, and AUU; Lysine (Lys, K) AAA and AAG; Leucine (Leu, L) UUA, UUG, CUA, CUC, CUG, and CUU; Methionine (Met, M) AUG; Asparagine (Asn, N) AAC and AAU; Proline (Pro, P) CCA, CCC, CCG, and CCU; Glutamine (Gln, Q) CAA and CAG; Arginine (Arg, R) AGA, AGG, CGA, CGC, CGG, and CGU; Serine (Ser, S) AGC, AGU, UCA, UCC, UCG, and UCU; Threonine (Thr, T) ACA, ACC, ACG, and ACU; Valine (Val, V) GUA, GUC, GUG, and GUU; Tryptophan (Trp, W) UGG; and Tyrosine (Tyr, Y) UAC and UAU.

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, and the like.

It also is understood in the art that the substitution of like amino acids can be made effectively on the basis of hydrophilicity. It is understood that an amino acid can be substituted for another having a similar hydrophilicity value and still produce a biologically equivalent protein.

As outlined above, amino acid substitutions generally are based on the relative similarity of the amino acid side-chain substituents, for example, their hydrophobicity, hydrophilicity, charge, size, and the like. Examples of substitutions that take into consideration the various foregoing characteristics are well known and include: arginine and lysine; glutamate and aspartate; serine and threonine; glutamine and asparagine; and valine, leucine and isoleucine.

Embodiments involve polypeptides, peptides, proteins and fragments thereof for use in various aspects described herein. In specific embodiments, all or part of proteins described herein can also be synthesized in solution or on a solid support in accordance with conventional techniques. Various automatic synthesizers are commercially available and can be used in accordance with known protocols. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions.

Also included are fusion proteins. Embodiments can include individual fusion proteins as a fusion protein with heterologous sequences such as a provider of purification tags, for example: β-galactosidase, glutathione-S-transferase, green fluorescent proteins (GFP), epitope tags such as FLAG, myc tag, or polyhistidine.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. As used herein an amino acid designated as "X" refers to any amino acid residue. However, when in the context of an amino acid substitution it is to be understood that "X" followed by a number refers to an amino acid residue at a particular location in a reference sequence.

As used herein, an amino acid residue of an amino acid sequence of interest that "corresponds to" or is "corresponding to" or in "correspondence with" an amino acid residue of a reference amino acid sequence indicates that the amino acid residue of the sequence of interest is at a location homologous or equivalent to an enumerated residue in the reference amino acid sequence. One skilled in the art can determine whether a particular amino acid residue position in a polypeptide corresponds to that of a homologous reference sequence. For example, the sequence of a modified or related Cas9 protein can be aligned with that of a reference sequence (e.g., SEQ ID NO: 1 using known techniques (e.g., basic local alignment search tool (BLAST), ClustalW2, Structure based sequences alignment program (STRAP), or the like). In addition, crystal structure coordinates of a reference sequence may be used as an aid in determining a homologous polypeptide residue's three dimensional structure. Using such methods, the amino acid residues of a polypeptide can be numbered according to the corresponding amino acid residue position numbering of the reference sequence. For example, the amino acid sequence of SEQ ID NO: 1 may be used for determining amino acid residue position numbering of each amino acid residue of a variant of interest.

The term "identical" in the context of two nucleic acids or polypeptide sequences refers to the residues in the two sequences that are the same when aligned for maximum correspondence, as measured using one of the following sequence comparison or analysis algorithms.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (see Altschul, et al., *J. Mol. Biol.,* 215:403-410 [1990]). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915 [1992]) alignments (B) of 50, expectation (E) of 10, M'5, N'-4, and a comparison of both strands.

The BLAST algorithm then performs a statistical analysis of the similarity between two sequences (see, e.g., Karlin and Altschul, supra). One measure of similarity provided by the BLAST algorithm is the smallest sum probability (P(N)), which provides an indication of the probability by which a match between two nucleotide or amino acid sequences would occur by chance.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference amino acid sequence means that the subject amino acid sequence is identical (i.e., on an amino acid-by-amino acid basis) by a specified percentage to the reference amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A. Results
HNH Domain Samples Larger Conformational Space in the Absence of ntDNA.

Figures 7A, 7B, 7C:
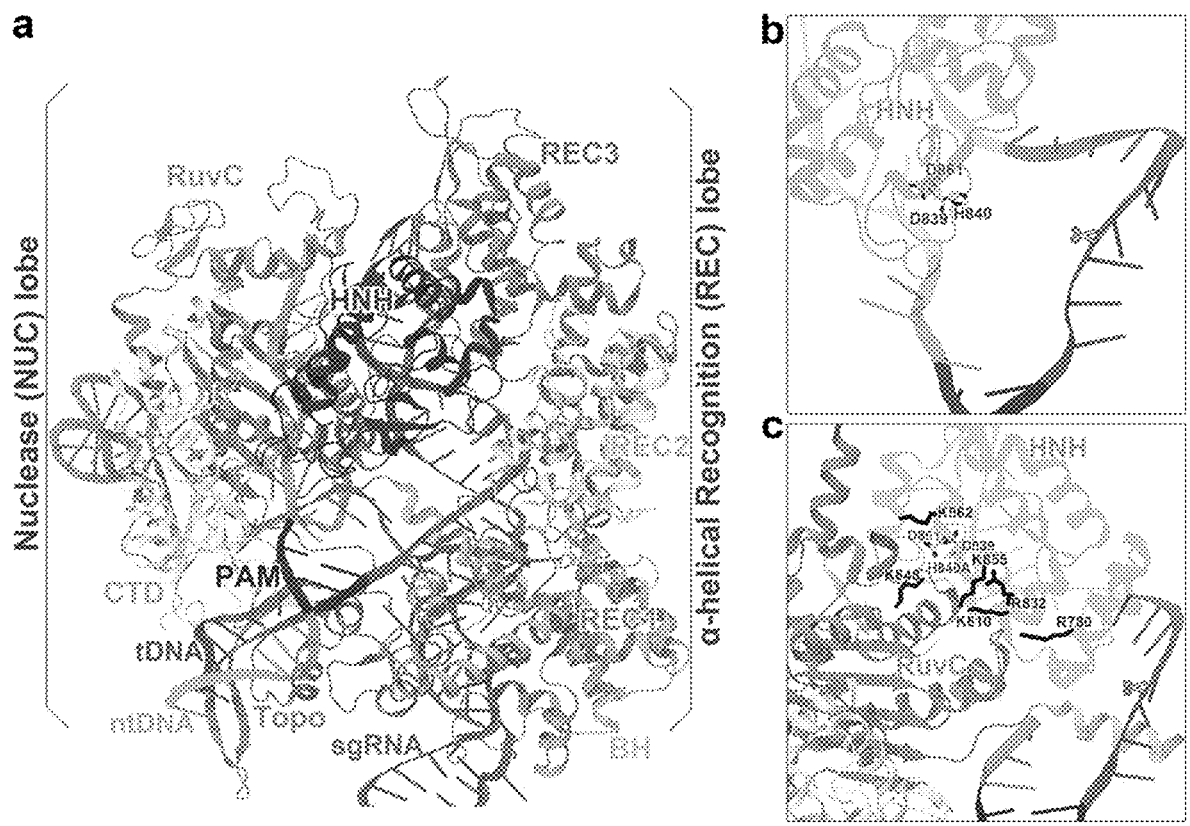
FIGS. 7a-7c. spCas9-sgRNA complexed with PAM-containing double-stranded DNA (dsDNA) substrate. (a) Overall architecture of the ternary complex of spCas9, sgRNA and dsDNA (PDB code: 5F9R). Cas9 NUC lobe comprises of two nuclease domains (RuvC and HNH), C-terminal domain (CTD) and topoisomerase homology (Topo) domain, and REC lobe is spatially divided into three domains (REC1, REC2 and REC3); the two lobes are connected by an arginine-rich (bridge) helix (BH). The target and non-target DNA strands (tDNA and ntDNA) are colored dark and light green, respectively, with the PAM duplex highlighted in crimson. (b) Close-up view of the HNH domain active center (PDB code: 5F9R). The putative catalytic residues are depicted in a stick model. (c) Structured-guided protein engineering to improve spCas9 specificity (PDB code: 4UN3). Neutralization of the selected basic residues on the HNH domain were shown to reduce spCas9 off-target effects while maintaining off-target activity. The cleavage site on tDNA is denoted with a scissor.

To obtain HNH domain active state from inactive state structure using molecular dynamics simulations, the biggest challenge is to sample enough conformational space in a reasonably short time-scale. From initial MD simulations and structural observation (Jiang et al. *Science* 351, 867-871, 2016; Zuo and Liu, *Sci. Rep.* 5, 2016), the inventors contemplated that the ntDNA might impose spatial constraints on the conformational dynamics of HNH domain in the pre-catalytic state (FIG. 7a). In other words, the HNH domain could exhibit enhanced flexibility in the absence of ntDNA, thereby increasing the probability to reach or get closer to the catalytic state. To confirm, the inventors performed three groups of long time-scale conventional MD (cMD) simulations starting from the pre-catalytic structure (Jiang et al. *Science* 351, 867-871, 2016), in which the ntDNA was removed (G1 and G2, Table 1) or retained (G9, Table 1). Meanwhile, the accelerated MD (aMD) method (Hamelberg et al. *J. Chem. Phys.* 120, 11919-11929, 2004; Pierce et al. *J. Chem. Theory Comput.* 8, 2997-3002, 2012) was implemented to enhance the sampling of the system without ntDNA at two different boost levels (G3 and G4, Table 1). The effective sampling time adds up to 14.3 as, including 11 is of cMD and 3.3 s of aMD.

Figures 1A, 1B, 1C, 1D:
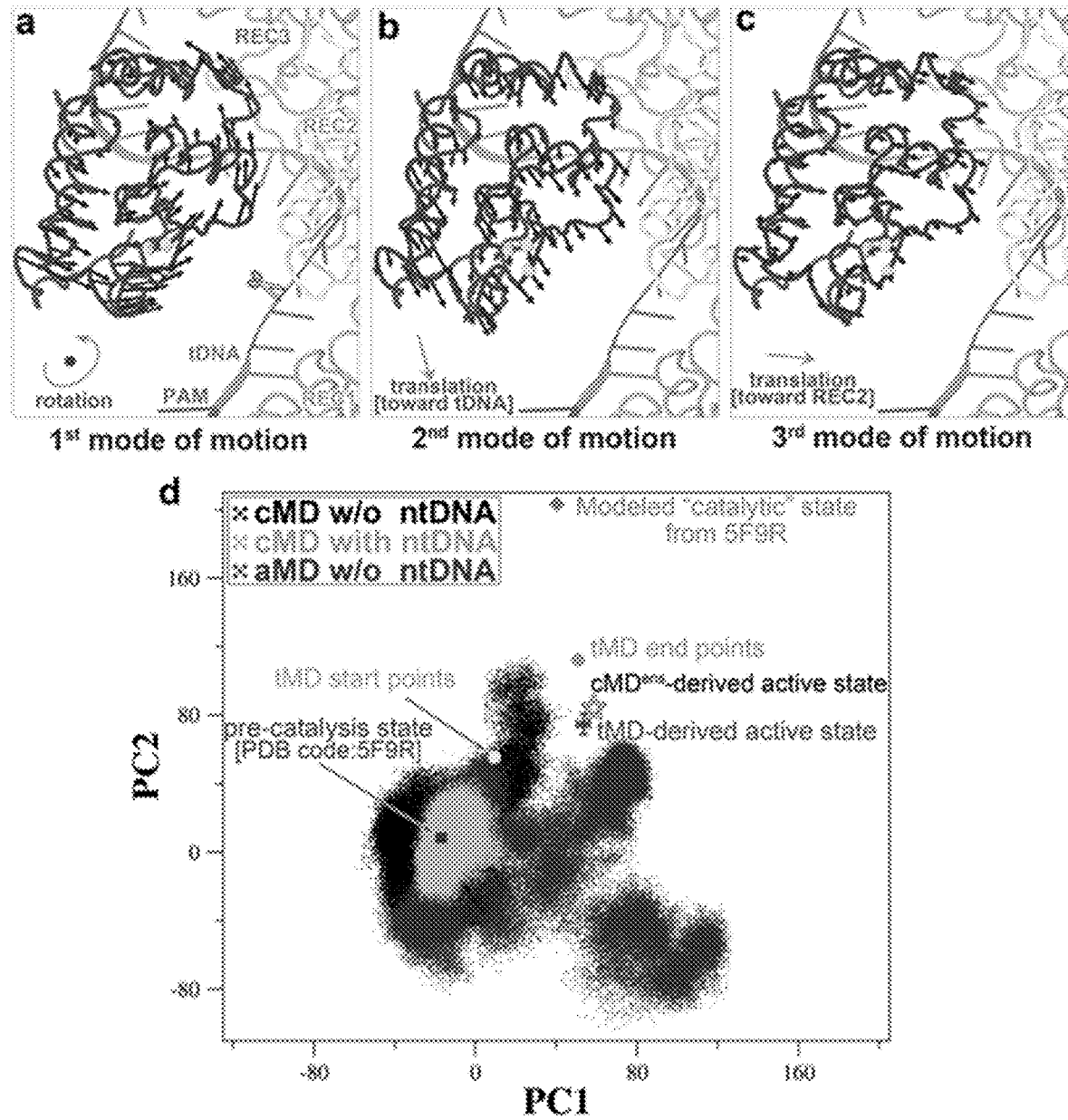
FIGS. 1a-1d. Cas9 HNH domain motions and conformational flexibility characterized by principal component analysis. (a-c) Visualization of the top three dominant motions for the HNH domain. The first motional mode depicts a rotation motion around an axis perpendicular to the plane, while the second and third modes describe a translational movement toward the tDNA and REC2 domain, respectively. The Cα atoms of the three HNH catalytic residues are represented as van der Walls spheres. (d) Overlap of the projections of the conventional MD simulations without ntDNA (cMD w/o ntDNA, blank dots), conventional MD simulations with ntDNA (cMD with ntDNA, green dots) and accelerated MD simulations without ntDNA (aMD w/o ntDNA, red dots) onto the first two eigen-vectors calculated from the whole trajectories for the HNH domain. The pre-catalytic state (PDB code: 5F9R), its modeled "catalytic" state from the crystal structure of T4 Endo VII complex with a DNA substrate, and the start and end points for the targeted MD (tMD) simulations were also projected onto the subspace defined by the first two PCA modes, along with the targeted MD (tMD)- and ensemble conventional MD (cMD$^{ens}$)-derived catalytic states (an average over 100 data points is reported). All the trajectories were best-fitted to the Cas9 protein (excluding the HNH domain) of the pre-catalytic crystal structure (PDB code: 5F9R), and the coordinate covariance matrix was computed over the HNH domain for subsequent analysis.

To compare the conformational spaces sampled with the two different systems and the two different simulation approaches, the inventors first performed the principal component analysis (PCA) to determine the dominant motions of the HNH domain. PCA is a multivariate statistical technique applied to systematically reduce the number of dimensions needed to describe protein essential dynamics (David and Jacobs, *Methods Mol. Biol.* 1084, 193-226, 2014; Amadei et al., *Proteins* 17, 412-425, 1993). The first three PCA modes, accounting for 70% (37%+23%+10%) of the overall motion, revealed a rotational motion along an axis perpendicular to the central channel between the two Cas9 lobes (FIG. 1a), and translational movements toward the tDNA (FIG. 1b) and the REC2 domain (FIG. 1c), respectively. Apparently, a combination of these dominant motions towards the REC lobe and tDNA would lead the HNH domain toward the cleavage site on the tDNA. Subsequently, the inventors projected individual sets of simulation trajectories onto the subspace defined by these three PCA vectors (FIG. 8a-8c). As contemplated, the accessible conformational space of the HNH domain in the ntDNA-bound system was approximately a subset of that in the ntDNA-free system (FIG. 1d and FIG. 8). Moreover, the distances of Ser867 (on HNH domain) to Ser355 (on REC1 domain) and to Asn1054 (on RuvC domain) that were selected for labeling in previous smFRET experiments were calculated (Dagdas et al., *bioRxiv*, 122242, 2017), and obtained similar results to the PCA (FIG. 9). In the inventors' dsDNA-bound model, the ntDNA 5'-end cleavage product was not included, and thus the sampling space is likely to be further confined in the context of full-length ntDNA due to interactions between the 5'-end stretch and HNH domain (Jiang et al., *Science* 351, 867-871, 2016; Zuo and Liu, *Sci. Rep.* 5, 2016; Palermo et al., *ACS Cent. Sci.,* 2016).

Compared to cMD, aMD explored much broader conformational space, especially along the first PC (FIG. 1d and FIG. 8) that depicts a rotation motion of the HNH domain (FIG. 1a). However, the third motional mode is more prominent in cMD than in aMD (FIG. 8f), suggesting the HNH domain displaying a larger-scale translation toward the REC lobe in cMD 5 (FIG. 1c).

Figure 10:
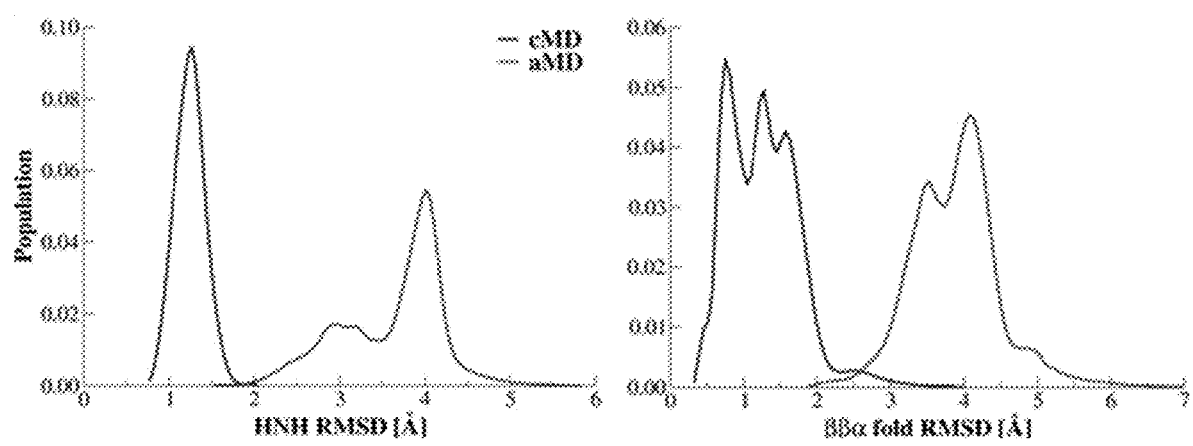
FIG. 10. Cα RMSD distributions for the HNH and ββα fold calculated from the conventional and accelerated MD simulations relative to the starting crystal structure (PDB code: 5F9R). The average pairwise RMSDs for the HNH domain and ββα motif among the available Cas9 crystal structures in different binding forms is 1.4±0.6 and 1.4±0.7 Å, respectively (Table 2a-2b), which are comparable to the corresponding peak values calculated from the cMD simulations. In contrast, aMD shows significantly larger RMSD values peaking at 4 Å, indicating the enhanced sampling accompanies considerable internal structural change.

To this end, the inventors demonstrated that HNH Domain samples larger conformational space in the absence of ntDNA and cMD is more appropriate in searching for HNH domain active state as aMD brings appreciable internal structural distortion (FIG. 10 and Table 2). As the microsecond time-scale samplings with cMD and aMD were unable to obtain an HNH conformation in sufficiently close proximity to the cleavage site on tDNA for catalysis, in the following sections, two different strategies to capture the converged catalytically active state of HNH domain are presented.

Targeted-MD Revealed the Catalytically Active State of HNH Domain.

One of the strategies used is the targeted MD (tMD) simulation (Schlitter et al., *J. Mol. Graphics* 12, 84-89, 1994; Schlitter et al., *Mol. Simul.* 10, 291-308, 1993). This approach can enable conformational transition between two known states by application of external forces. First, homologous T4 Endonuclease VII (Endo VII) complex with a DNA Holliday junction (Biertumpfel et al., *Nature* 449, 616-U614, 2007) were selected as the template to build the target conformation of HNH domain, which is the putative "active" conformation model (FIG. 11). Instead of a single static target, multiple targets were built based on each snapshot structure from the above sets of long cMD simulations. A snapshot structure was selected with a minimum root-mean-square deviation (RMSD) (~10 Å) from its own "target" as the starting point of the tMD. With a small force constant and a low RMSD decreasing rate, tMD simulations were carried out and observed the expected conformational transition of HNH domain, largely due to its intrinsic global flexibility as well as internal structural rigidity (FIG. 10 and Table 2). In the framework of one-metal-ion mechanism (FIG. 2d)(Yang, *Q. Rev. Biophys.* 44, 1-93, 2011; Yang, *Nat. Struct. Mol. Biol.* 15, 1228-1231, 2008), one $Mg^{2+}$ was then introduced at the reaction interface between the HNH domain and tDNA. After performing thorough post tMD simulations using conventional MD (G6, Table 1), a reasonable catalytically active conformation was obtained.

Figures 2A, 2B, 2C, 2D:
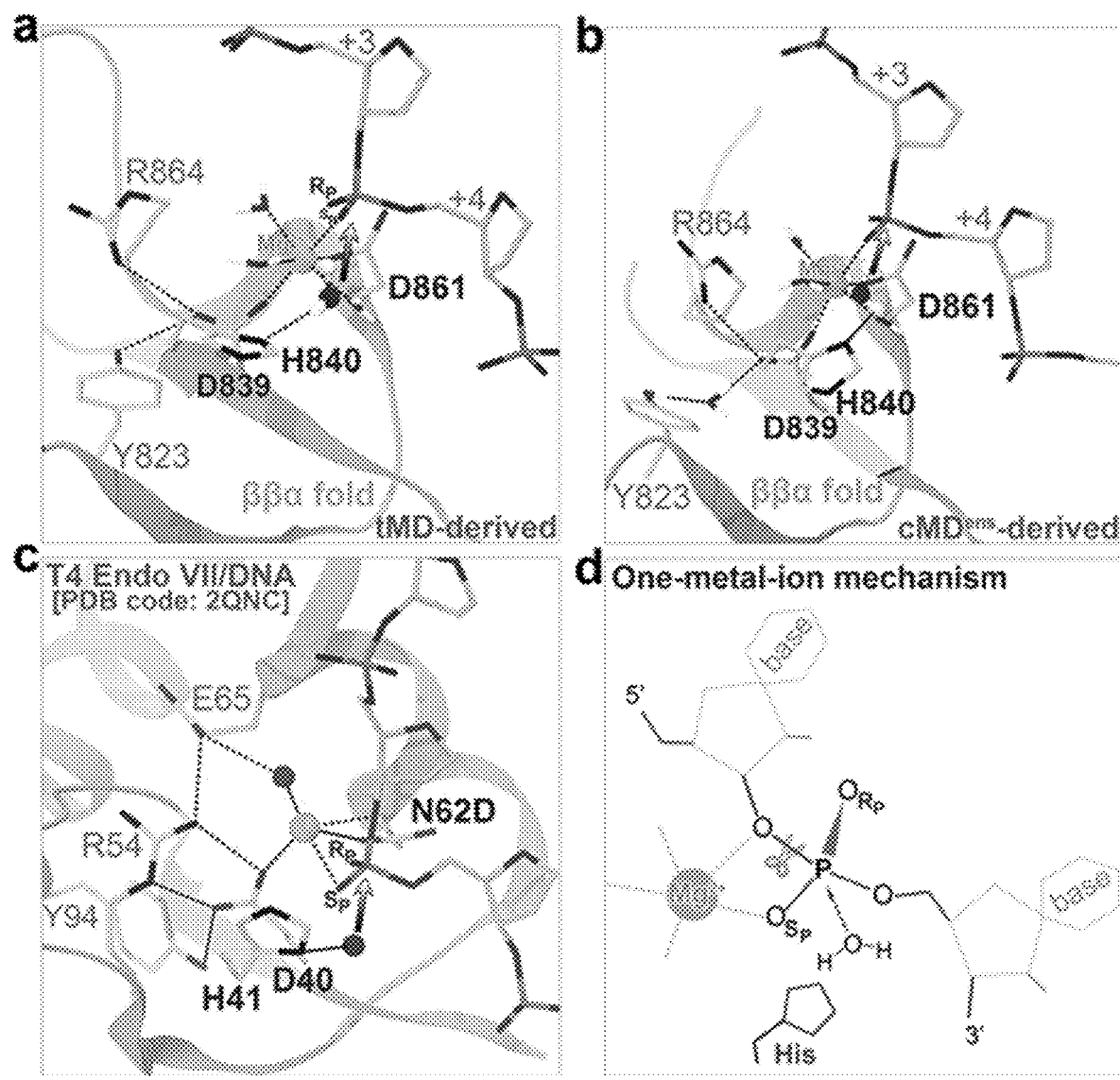
FIGS. 2a-2d. Catalytic state coordination at the interface of HNH ββα fold and tDNA (a,b) and comparison with the one-metal-ion catalysis by T4 Endo VII (c). (a,b) The representative coordination configurations derived from post targeted MD (tMD) simulations (a) and conventional ensemble MD (cMD$^{ens}$) simulations (b) through cluster analysis. (c) Close-up view of the active center of T4 Endo VII (N62D) resolving a DNA Holliday junction (PDB code: 2QNC). (d) Schematic representation of the one-metal-ion dependent catalysis in ββα-metal nucleases. The pro-Sp and pro-Rp oxygens of the scissile phosphate are indicated with Sp and Rp, respectively. The putative active residues in Cas9 HNH domain and the corresponding residues in T4 Endo VII are labeled in boldface. Mg$^{2+}$ is shown as a cyan sphere and the potential nucleophilic water is denoted by an arrow. The dashed lines indicate the coordination bonds involving Mg$^{2+}$ and hydrogen-bonds.
Figure 12:
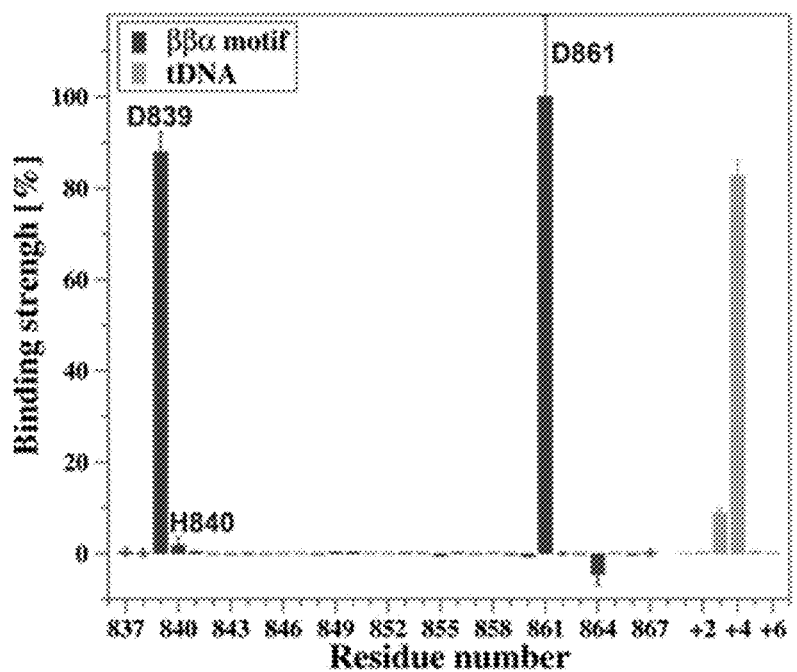
FIG. 12. Relative binding strength of the residues on the HNH ββα fold and opposite tDNA with the coordinated Mg2+ computed via MM-GBSA approach. The energetic contribution of each residue is relative to Asp861 being of 100% binding strength. Positive and negative values indicate favorable and unfavorable binding, respectively.

The $Mg^{2+}$ at the catalytic center formed a favorable octahedral coordination with six surrounding oxygen atoms from different species (FIG. 2a). In addition to the three water molecules, the residues Asp839 and Asp861 on the ββα motif and the scissile phosphate (pro-Sp oxygen involved) between the nucleotides +3 and +4 of tDNA each contributes a coordination ligand (FIG. 2a). The above observation is consistent with the per-residue energy decomposition data by MM-GBSA approach (FIG. 12), confirming the role of the residues in stabilizing $Mg^{2+}$. In contrast, His840 contributes marginally to $Mg^{2+}$ binding, which is in line with its major role as the general base activating the nucleophile. Notably, the His840 side chain hydrogen-bonded to a potential nucleophilic water molecule that is aligned for in-line attack on the scissile bond. Specially, Tyr823 and Arg864 appeared to play a structural role in stabilizing the catalytic Asp839 side chain by hydrogen-bonding. Such interactions were presumed to aid proper orientation of Asp839 for coordination and catalysis. Indeed, the amino acid Tyrosine is strictly conserved among different types of CRISPR-Cas9 by primary sequence analysis, while the basic amino acid Arginine (or Lysine) is highly conserved among the Type II-A Cas9 orthologs (Jinek et al., Science 343, 1247997, 2014).

Figures 3A, 3B, 3C, 3D:
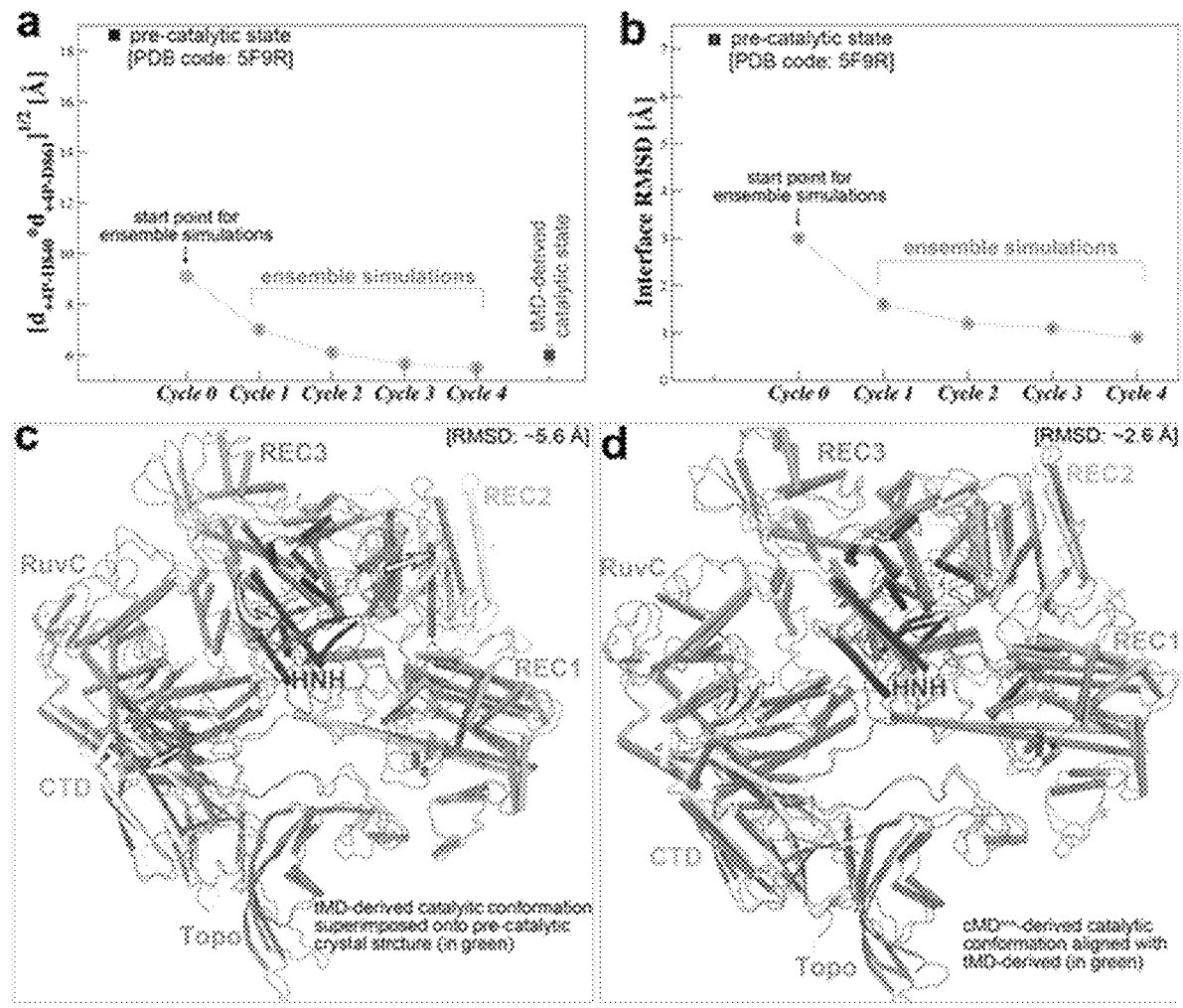
FIGS. 3a-3d. Comparison of the targeted MD (tMD)-derived and ensemble conventional MD (cMD$^{ens}$)-derived catalytic Cas9 conformations and Comparison with the crystal structure in pre-catalytic state. (a) Variation of the minimum geometric mean of the distances of +4P to His840 (d$_{+4P-H840}$) and to Asp861 (d$_{+4P-D861}$) as a function of the cycle number in the course of the ensemble simulations. (b) Variation of minimum binding interface RMSDs from the tMD-derived catalytic state as the cycle number increases. An average over fifty data points is reported in a and b. (c) Structural superposition between the tMD-derived catalytic state and crystal pre-catalytic state (PDB code: 5F9R). The crystal structure is represented and the largest domain movement (involving HNH, CTD and REC2) is denoted by a arrow. See also FIG. 13 for the result with cMD$^{ens}$. (d) Structural alignment between the tMD- and cMD$^{ens}$-derived catalytic Cas9 conformations.

Overall, the three active resides Asp839, His840 and Asp861, and the other two residues, Tyr823 and Arg864 (FIG. 2a), are spatially and functionally analogous to the corresponding residues, Asp40, His41, Asn62, Tyr94 (on the other subunit) and Arg54, in the T4 Endo VII (FIG. 2c) (Biertumpfel et al., Nature 449, 616-U614, 2007). Despite the similarities, the $Mg^{2+}$ here was not positioned so proximal to the leaving group 3'-O as in the Endo VII system (Biertumpfel et al., Nature 449, 616-U614, 2007), which was also observed at the reaction interface between the Cas9 RuvC domain and ntDNA in a prior inventor study with the same force fields (Zuo and Liu, Sci. Rep. 5, 2016). Apart from the potential issue with $Mg^{2+}$ parameters, this deviation might be partly related to the subtle differences between the two enzymes beyond the coordination center. In Endo VII, for instance, there exists an additional acidic residue (Glu65) hydrogen-bonded to a coordinating water molecule above the bound $Mg^{2+}$ (FIG. 3c). In summary, the coordination composition and geometry captured here closely match those present in the T4 Endo VII/DNA complex, indicating the formation of catalytically active state of Cas9 HNH domain and consistent with previously identified tDNA cleavage site being of 3 nucleotides from the PAM (Jinek et al., Science 337, 816-821, 2012; Gasiunas et al., Proc. Natl. Acad. Sci. U.S.A. 109, E2579-2586, 2012).

Conventional Ensemble MD Simulations Revealed the Same Catalytic State as tMD Derived.

Figures 4A, 4B, 4C:
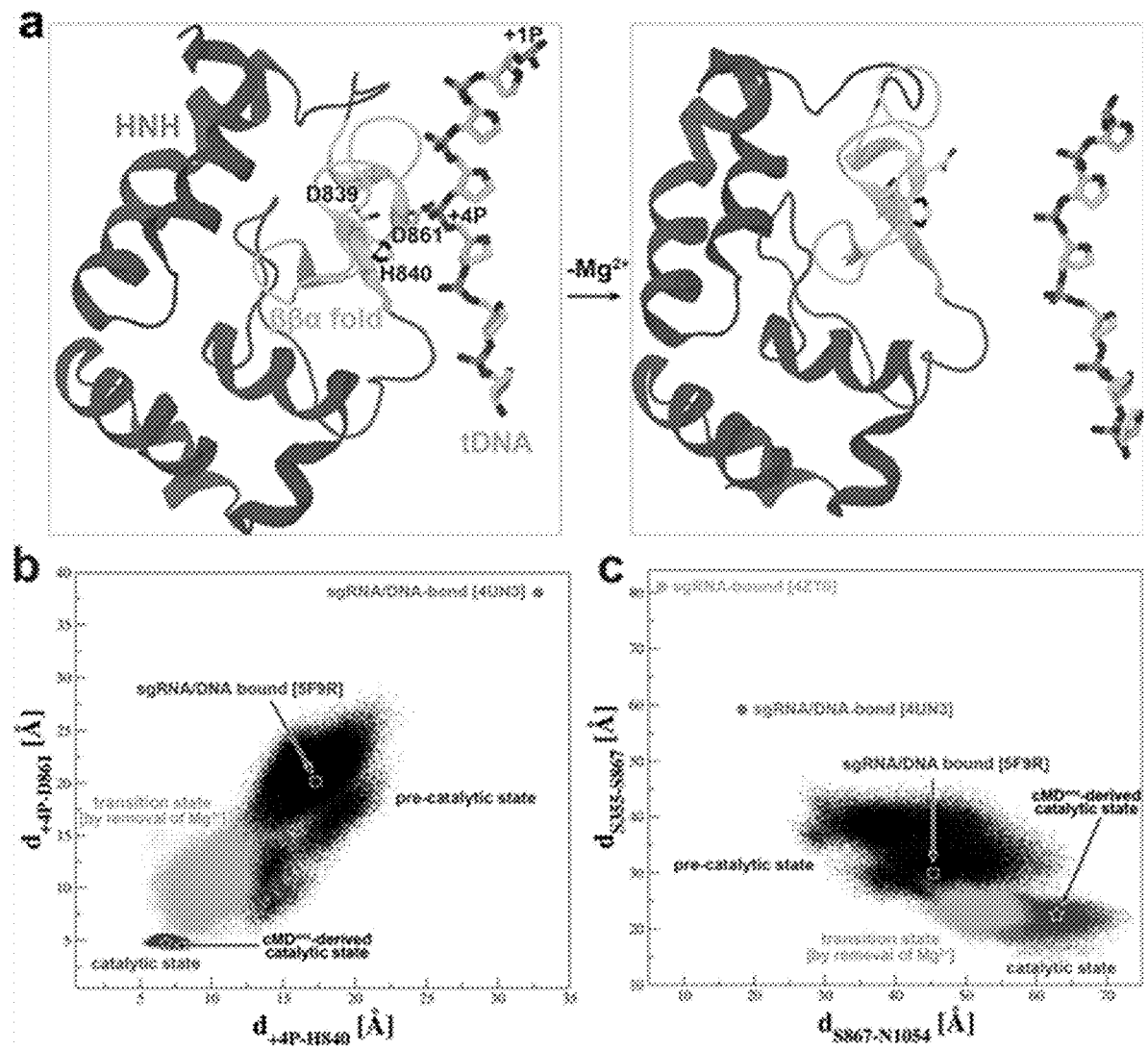
FIGS. 4a-4c. Mg$^{2+}$-aided conformational transition to catalytic state. (a) Comparison of the representative HNH conformations from the cMD simulations with Mg$^{2+}$ bound (left) and with Mg$^{2+}$ removed (right) at the reaction interface. The bound Mg$^{2+}$ is shown as a sphere and the HNH active residues are represented in a stick model. (b) Scatter plot of the +4P distances to His840 (d$_{+4P-H840}$) and Asp861 (d$_{+4P-D861}$) calculated from different sets of cMD simulations. The Cγ and P atoms were selected for measurement. (c) Scatter plot of the distance pair for Ser867/Asn1054 (ds867-N1054) and Ser355/Ser867 (ds355-867) from different sets of cMD simulations. The Cα atoms were calculated here. The residue pairs of Ser867/Asn1054 and Ser355/Ser867 were used to characterize the conformational states of HNH domain in previous FRET experiments (FIG. 9). If available, the corresponding distance pairs obtained from different Cas9 complex crystal structures are mapped on each plot. Of note, in 4UN3, the loop where Asn1054 resides is disordered and we report an average of the distances calculated from respective modeled structures using 4ZT0, 4ZT9 and 5F9R as a template. The pentagrams indicate the catalytic state derived from the conventional ensemble MD (cMD$^{ens}$) simulations (an average over 100 data points is reported).

The above tMD-based strategy to capture the catalytic state in essence is based on a modeled putative "target" state. Although the building process was treated with special considerations, the potential artificial effects underlying the tMD-derived catalytic model cannot be definitely ruled out. Therefore, the inventors performed a series of conventional MD ensemble simulations ($cMD^{ens}$) starting from the original pre-catalytic crystal structure (PDB code: 5F9R) to check if the same catalytic state could be reached using the unbiased MD approach. The inventors developed a method called "Step-by-step MD". The basic idea behind this method is to extract the structure that mostly resembles the active state from a set of MD simulations as the new starting point for a new set of the simulations. Step by step, one can efficiently sample the desired conformational space without any artificial forces. As the actual catalytic state is not known, it is challenging to choose the structure that mostly resembles the catalytic state. Here, the inventors used the geometric mean of the distances of +4P (the scissile phosphate) to two catalytic residues His840 and Asp861 (FIG. 4a) as a metric to monitor the conformational transition of HNH domain. Apparently the smaller this value is, the closer the conformation is to the target active conformation (FIG. 4b). From the sets of long cMD trajectories (G1 and G2, Table 1), a structure bearing a minimum value of ~9 Å was extracted as the starting point for the ensemble simulations (FIG. 3a), where one $Mg^{2+}$ was located at the reaction center. In each cycle, the ensemble simulations were seeded from a structure snapshot from previous cycle bearing a lowest value of the above geometric mean (FIG. 3a), which is the core of the sampling approach here.

Through four cycles (G8.1-G8.4, Table 1), the above geometric mean stabilized at ~6 Å (FIG. 3a), which is comparable to that observed for the tMD-derived catalytic state (FIG. 4b). Accordingly, the RMSD of the reaction interface from the tMD-derived catalytic state declined from initial ~3 Å to ~1 Å (FIG. 3b). Moreover, the $Mg^{2+}$-involved coordination composition and configuration here (FIG. 2b) are essentially the same to those derived from tMD (FIG. 2a), except that Tyr823 was engaged to Asp839 via an intercalated water molecule, again confirming the structural role of Tyr823 around the reaction center. These observations therefore demonstrated formation of the $cMD^{ens}$-derived catalytic state.

Figure 13:
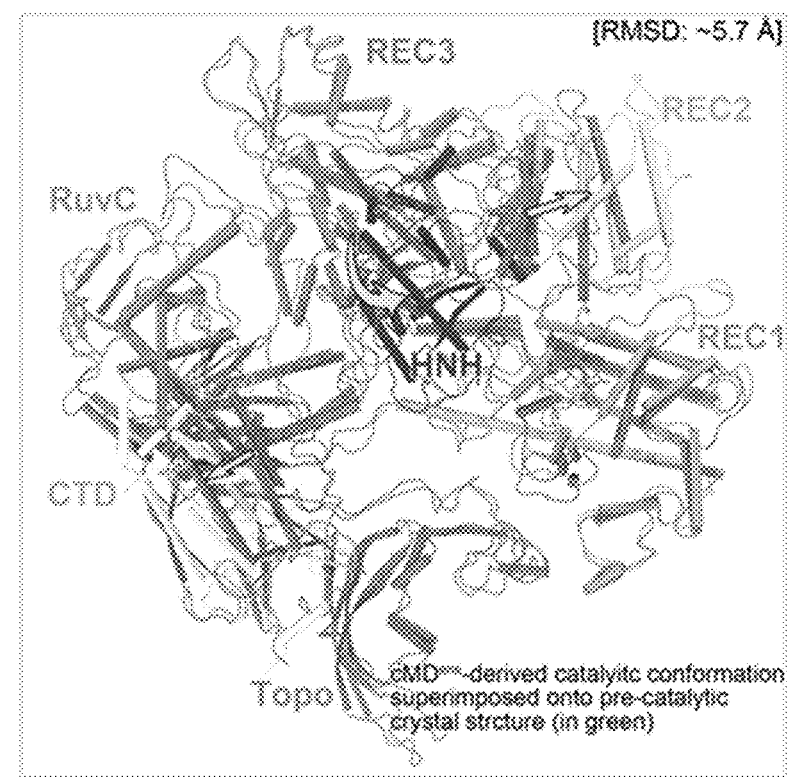
FIG. 13. Structural superposition between the cMDens-derived catalytic state and crystal pre-catalytic state (PDB code: 5F9R). The crystal structure is represented, and the largest domain movement (involving HNH, CTD and REC2) is dented by an arrow. This figure is comparable to FIG. 3c.

With the active state formation, the Cas9 protein underwent prominent conformational changes, as observed from either of the post tMD and $cMD^{ens}$ simulations. The overall Cα RMSD from the initial crystal structure is near to 6 Å, in which the HNH domain displayed a largest RMSD of ~11 Å as expected, followed by the CTD and REC2 domains with a RMSD around 7~8 Å (Table 3). In the absence of ntDNA, the CTD domain moved outward markedly, resulting in wide opening of the side channel within the NUC lobe poised for substrate loading (FIG. 3c and FIG. 13). When RMS fitting to themselves, the HNH and REC2 domains exhibited a much smaller RMSD of less than 2 Å (Table 3), indicating concerted motion of REC2 domain with the HNH domain. By contrast, the RMSD of CTD domain was down by a relatively small range of 3.5 Å, suggesting considerable variation in its internal conformation in addition to the above large-scale reorientation. Taken together, the results reveal the highly mobile nature of individual Cas9 domains, consistent with previous experimental and computational studies (Jiang et al., Science 351, 867-871, 2016; Jiang et al., Science 348, 1477-1481, 2015; Nishimasu et al., Cell 156, 935-949, 2014; Anders et al., Nature 513, 569-573, 2014; Jinek et al. Science 343, 1247997, 2014; Palermo et al., ACS Cent. Sci., 2016).

Overall, the two different derived catalytic conformations were well superimposable (FIG. 3d). The global RMSD between them is around 2.6 Å (Table 3), partly contributed by the flexible CTD domain and relative domain movements. In line with these results, the HNH domain assumed a similar orientation and conformational state between the two catalytic states, as characterized by the principal component analysis (FIG. 1d) and the distance pair between the FRET-labeled residues (FIG. 4c). Furthermore, the vast majority of newly formed interactions with the HNH domain are common between the two catalytic conformations (FIG. 5, FIG. 14 and Table 4) as mentioned below. In aggregate, all these data suggest good convergence of the tMD- and $cMD^{ens}$-derived catalytic models.

$Mg^{2+}$ is Indispensable for Activation of the Catalytic State.

The inventors' previous work with Cas9 RuvC domain revealed that $Mg^{2+}$ is able to induce the formation of the active state for cleaving the ntDNA (Zuo and Liu, *Sci. Rep.* 5, 2016). Likewise, beyond its catalytic role, $Mg^{2+}$ could also facilitate conformational activation of the HNH domain. To confirm, the inventors removed the coordinated $Mg^{2+}$ from the above catalytic conformation (FIG. 2a) and performed microsecond-level conventional MD simulations (G7, Table 2). In the absence of $Mg^{2+}$, two distinct consequences on the HNH domain are envisioned, i.e., either departing from the tDNA or staying docked at the tDNA without noticeable reorganization.

The inventors first monitored the changes in the distance pair of +4P to His840 ($d_{+4P-H840}$) and to Asp861 ($d_{+4P-D861}$) at the cleavage interface (FIG. 4a). Their geometric mean increased from 6.0 Å in the catalytic state simulations to 10.5 Å on average, indicating detachment of the HNH domain from the tDNA. Further comparison with the cMD simulations starting from the pre-catalytic state clearly showed that absence of $Mg^{2+}$ leads the HNH domain to a transition state between the catalytic and pre-catalytic state (FIG. 4b). The inventors contemplated that with a longer sampling time, the HNH domain would ultimately reach the pre-catalytic state as observed in the crystal structure (Jiang et al., *Science* 351, 867-871, 2016). A similar trend was also observed with the FRET residue pairs (Ser867/Asn1054 and Ser355/Ser867)(FIG. 4c), yet the states are relatively less distinguishable than with the reaction interfacial residues (FIG. 4b), probably due to a longer time needed for remote conformational relaxation. Consequently, the binding free energy of Cas9 to tDNA reduced by ~30 kcal/mol compared to the catalytic state (not including the entropic contribution). More specially, the non-bonded interaction energy of the HNH ββα motif with the scissile phosphate and flanking nucleotides decreased by ~64 kcal/mol. Given the stable $Mg^{2+}$-mediated catalytic conformation, the inventors argue that the HNH domain are least likely separated from its opposite cleavage site unless the reaction is over. Taken together, these results provide evidence that $Mg^{2+}$ is essential for the formation and stability of Cas9 HNH domain active state, as observed for the RuvC domain (Zuo and Liu, *Sci. Rep.* 5, 2016). The findings here are in good accordance with the most recent smFRET experiments (Dagdas et al., *bioRxiv*, 122242, 2017).

The Catalytic State Provides New Structural Information for Specificity Enhancement.

Accompanying the active state formation, remarkably, the HNH domain established a plenty of new interactions with the REC lobe (including REC1, REC2 and REC3), bridge helix (BH), tDNA and sgRNA, predominantly involving the charged and polar residues (FIG. 5, FIG. 14 and Table 4). In detail, the two basic residues of HNH ββα motif, Lys862 and Lys866, formed alternative ionic interactions with the three acidic residues Glu370, Glu371 and Glu396 on REC1, respectively (FIG. 5a and FIG. 14a). Meanwhile, Lys775, Arg778 and Glu779 (on HNH flanking linker 1, L) competed for binding to Glu584, Asp585, Arg586 and Lys558 of REC3, respectively (FIG. 5c and FIG. 14c). The HNH loop immediately preceding the ββα motif made numerous side chain and backbone hydrogen bonds with REC2, such as Asn831 with Thr249/Asn251, and Ser834 with Gly247/Thr249 (FIG. 5b and FIG. 14b). Interestingly, Asp835 alone hydrogen-bonded to one helical turn of Ser217, Lys218 and Ser219 on REC2. Additionally, Arg832 and/or Arg859 (on ββα motif) formed charged interactions with the REC2 Glu223 (FIG. 5b and FIG. 14b). Lying on the long loop between the two 0 elements of ββα motif, Gln844 and Lys848 were engaged to Glu60 on BH and Thr58 (on the loop linking BH and RuvC) via hydrogen-bond and ionic interactions, respectively (FIG. 5d and FIG. 14d). Another adjacent residue Ser845 was implicated in hydrogen-bonding to the +3P of tDNA, a position only 1-nt from the cleavable site (FIG. 5e and FIG. 14e). Also, the HNH domain formed a number of polar contacts with the backbone of sgRNA (primarily at its middle guide segment). Located on the N-terminal ββα motif flanking helices, the residue pair of Asn803 and Gln807, and the triplet of Arg780, Arg783 and Tyr812 firmly caught the two nucleotides 8 and 9 of sgRNA (numbered 1 from the most PAM-distal end), respectively, through hydrogen-bonds and/or salt bridges (FIG. 5f and FIG. 14f). Meanwhile, the two basic residues, Lys848 and Arg895 (on the last C-terminal ββα motif flanking helix) participated in ionic interactions with the trinucleotide stretch from sites 11 to 13 (FIG. 5d and FIG. 14d). Along with $Mg^{2+}$, the identified Cas9 residues above definitely play a crucial role in locking the HNH domain onto the scissile phosphate on tDNA.

The structural information derived here can be exploited to minimize the off-target effects of CRISPR-Cas9. Guided by the "excess energy" hypothesis that Cas9-sgRNA is more energetic than needed for its optimal on-target recognition and cleavage, two recent works (Slaymaker et al., *Science* 351, 84-88, 2016; Kleinstiver et al., *Nature* 529, 490-495, 2016) reported several versions of high-fidelity Cas9 variants bearing multiple alanine substitutions, which were engineered based solely on an inactive DNA-bound crystal structure available at that time. The inventors noticed that there are four basic residues on the HNH domain (viz. Lys775, Arg832, Lys848 and Lys862) identified here that have been experimentally touched (FIG. 7c)(Slaymaker et al., *Science* 351, 84-88, 2016). Neutralization of these residues were demonstrated to improve Cas9 specificity in varying degrees, in which the single K848A mutant performed best exhibiting remarkably reduced off-target cleavage at all tested sites while maintaining on-target efficiency (Slaymaker et al., *Science* 351, 84-88, 2016). From the catalytic Cas9 structure, K848A conversion could destabilize the activated conformation of HNH domain due to disruption of favorable interactions with the BH and sgRNA (FIG. 5d and FIG. 14d), thereby requiring more stringent canonical basing paring between the guide RNA and tDNA. With the new structural information, likewise, more Cas9 nucleases with enhanced specificity can be rationally designed by trying different single and combined mutations.

B. Methods

System Setup.

The initial configurations of the two Cas9 complex systems, viz. Cas9-sgRNA-dsDNA (with tDNA) and Cas9-sgRNA-tDNA (without ntDNA) were derived from the recently solved crystal structure at 3.4 Å resolution (PDB accession code: 5F9R (Jiang et al., *Science* 351, 867-871, 2016)). The ntDNA-free system was built by removing the entire non-target DNA strand from the intact structure, while for the dsDNA-bound system, the ntDNA 5'-end cleavage product was excluded based on previous study (Zuo and Liu, *Sci. Rep.* 5, 2016). Following the two-metal-ion and one-metal-ion mechanisms proposed for Cas9 (Jiang et al., *Science* 351, 867-871, 2016; Nishimasu et al., *Cell* 156, 935-949, 2014; Jinek et al., *Science* 343, 1247997, 2014), two $Mg^{2+}$ were placed around the RuvC active center with partial ntDNA or without ntDNA, and if applicable, one $Mg^{2+}$ was introduced at the HNH active center (Table 1), as previously described (Zuo and Liu, *Sci. Rep.* 5, 2016). The missing heavy atoms and hydrogen atoms were added using leap program within AmberTool16 (Salomon-Ferrer et al., *Wiley Interdiscip. Rev. Comput. Mol. Sci.* 3, 198-210, 2013)

and the protonation states of protein titratable residues were assigned through the on-line tool H++ at a physiological pH of 7.5 (Gordon et al., *Nucleic Acids Res.* 33, W368-371, 2005), followed by visual check. Each system above was then immersed in a cubic water box with a thickness of 13.5 Å, leading to a simulation cell of approximately 139×124× 187 Å$^3$. To mimic the reaction buffer (Jinek et al., *Science* 337, 816-821, 2012; Jinek et al., *Science* 343, 1247997, 2014; Sternberg et al., *Nature* 507, 62-67, 2014; Sternberg et al., *Nature* 527, 110-113, 2015), extra 7 or 8 Mg$^{2+}$ were added into the water box to yield a concentration of 5 mM, and the ionic strength of KCl was set to 100 mM. The total atoms of Cas9-sgRNA-dsDNA and Cas9-sgRNA-tDNA solution systems add up to ~283,500 and ~281,800, respectively.

algorithm (Miyamoto and Kollman, *J. Comput. Chem.* 13, 952-62, 1992). Each system was subjected to a thorough energy minimization with the solute heavy atoms constrained, then followed by slow heating from 0 K to the target 310.15 K and 10-ns equilibration in the isothermal-isochoric (NVT) ensemble in which the backbone atoms were restrained. Finally, the production simulations (i.e. G1, G2 and G9 in Table 1) without any restraints were conducted under the isothermal-isobaric (NpT) condition and each independent run was extended to at least 1000 ns. The temperature was maintained at 310.15 K through the Langevin thermostat and the pressure was controlled at 1.013 bar via the Monte Carlo barostat. The integration time step was set to 1 fs during minimization and equilibration, and 2

TABLE 1

Summary of MD simulations for Cas9 complex systems without non-target DNA strand (w/o ntDNA) and with ntDNA

|  | Group | Simulation method* | Starting structure | Production time per run [ns] | No. of runs | Mg$^{2+}$ present at HNH domain? |
|---|---|---|---|---|---|---|
| w/o ntDNA | G1 | cMD | Crystal structure (PDB code: 5F9R) | 2500 | 2 | |
|  | G2 |  |  | 1000 | 1 | ✓ |
|  | G3 | aMD$^{Ed}$ | Extracted from G1 | 650 | 2 | |
|  | G4 | aMD$^{dual}$ |  | 1000 | 2 | |
|  | G5 | tMD | Extracted from G1/G2 | 100 | 2 | |
|  | G6 | cMD | Extracted from G5 | 800 | 2 | ✓ |
|  | G7 | cMD | Extracted from G6 | 800 | 2 | |
|  | G8.1 | cMD$^{ens}$ | Extracted from G1/G2 | 500 | 10 | ✓ |
|  | G8.2 |  | Extracted from G8.1 |  | 10 | ✓ |
|  | G8.3 |  | Extracted from G8.2 |  | 10 | ✓ |
|  | G8.4 |  | Extracted from G8.3 |  | 10 | ✓ |
| with ntDNA | G9 | cMD | Crystal structure (PDB code: 5F9R) | 1000 1500 | 2 2 | |

*cMD, conventional unbiased MD; aMD$^{Ed}$, accelerated MD with dihedral boost only; aMD$^{dual}$, accelerated; MD with simultaneous dihedral and total potential boost, tMD, targeted MD; cMD$^{ens}$, ensemble cMD.

Conventional Molecular Dynamics Simulations.

All kinds of simulations were performed by the GPU version of AMBER16 pmemd engine (pmemed.cuda)(Salomon-Ferrer et al., *Wiley Interdiscip. Rev. Comput. Mol. Sci.* 3, 198-210, 2013) except the targeted MD simulations that were realized with NAMD2.10 (Phillips et al., *J. Comput. Chem.* 26, 1781-1802, 2005)(as described below). The amber force fields ff14SBonlysc, ff99bsc0 and ff99bsc0_chiOL3 were used to describe paired interactions involving protein, DNA and RNA, respectively. The TIP3P model (Jorgensen et al., *J. Chem. Phys.* 79, 926-35, 1983) was selected for water and the recently developed ion parameter sets optimized in TIP3P water were employed for the mono- and divalent ions (Li et al., *J. Chem. Theory Comput.* 11, 1645-57, 2015; Li et al., *J. Chem. Theory Comput.* 9, 2733-48, 2013). It should be mentioned that none of the available non-bonded models for metal ions, especially the multivalent ions, is able to reproduce various experimental properties simultaneously (Panteva et al., *J. Comput. Chem.* 36, 970-82, 2015); the Mg$^{2+}$ parameter set here, as previously used for the same enzyme (Zuo and Liu, *Sci. Rep.* 5, 2016), represent the best possible compromise targeting the experimental coordination number, Mg$^{2+}$—O distance and hydration free energy (Li et al., *J. Chem. Theory Comput.* 9, 2733-48, 2013). The short-range non-boned interaction were truncated at 10 Å, and the long-range electrostatics were treated via the particle mesh Eward summation (PME) method (Darden et al., *J. Chem. Phys.* 98, 10089-92, 1993) using a grid spacing of 1 Å. The bonds involving hydrogens were constrained through the SHAKE fs in the production stage. The trajectory snapshots were saved at 10-ps intervals for analysis.

Accelerated Molecular Dynamics (aMD).

aMD is an enhanced sampling technique by adding a non-negative potential [$\Delta V(r)$] to the original potential energy surface [$V(r)$] when it falls below a threshold energy (E), as $$\Delta V(r) = \begin{cases} 0 & V(r) \geq E \\ \dfrac{(E - V(r))^2}{\alpha + (E - V(r))} & V(r) < E \end{cases} \quad (1)$$

where the acceleration factor $\alpha$ modulates the depth and local roughness of the energy basins in the modified potential (Hamelberg et al., *J. Chem. Phys.* 120, 11919-29, 2004; Pierce et al., *J. Chem. Theory Comput.* 8, 2997-3002, 2012). Apparently, this simple formalism has several practical advantages: only two parameters (E, $\alpha$) need to be specified and an a prior reaction coordinate is not required to be defined. Here, two acceleration levels were applied to the Cas9-sgRNA-ntDNA system, i.e., boosting only the dihedral energy terms (dihedral aMD) and boosting the whole potential with an extra boost to the dihedrals (dual aMD) (G3 and G4, Table 1). Following previous works (Pierce et al., *J. Chem. Theory Comput.* 8, 2997-3002, 2012; de Oliveira et al., *PLoS Comput. Biol.* 7, e1002178, 2011), the boosting parameters for each aMD run were estimated from the corresponding 60-ns conventional MD simulations carried out in the NVT ensemble. The aMD simulations were started from the last snapshots of the above short cMD simulations and were performed also in NVT ensemble, lasting 650 ns and 1000 ns for the dihedral and dual modes, respectively (G3 and G4, Table 1). In preliminary tests, the new variant GaMD (Gaussian accelerated MD) were run (Miao et al., *J. Chem. Theory Comput.* 11, 3584-3595, 2015) that allows for improved reweighting. In results, appreciable loss of protein secondary structures were found, thereby not applying this approach herein.

Targeted Molecular Dynamics (tMD).

tMD induces conformational transition between two known states by means of steering forces (Schlitter et al., *J. Mol. Graphics* 12, 84-89, 1994; Schlitter et al., *Mol. Simul.* 10, 291-308, 1993). At each time step, the root-mean-square deviation (RMSD) between the current coordinates and the target structure is calculated. The force exerted on each atom is given by the gradient of the potential, $$U_{tMD} = \frac{1}{2}\frac{k}{N}[RMSD(t) - RMSD^*(t)]^2 \quad (2)$$

where the spring constant k is scaled down by the number N of targeted atoms, RMSD (t) is the instantaneous best-fit RMSD of the current coordinates from the target conformation, and RMSD*(t) evolves linearly from the initial RMSD at the first tMD step to the final value at the last step. The two start structures for tMD were extracted from the replicated long cMD simulations (Table 1), based on the HNH domain closeness to the putative catalytic state modeled from the crystal structure of T4 endonuclease VII (Endo VII) complexed with a DNA Holliday junction (See below and FIG. 11)(Biertumpfel et al., *Nature* 449, 616-U614, 2007). The guiding forces were imposed only on the backbone atoms of HNH domain. The initial RMSDs of the biased atoms from the target states are around 10 Å, which are significantly lowered compared with that of 25 Å calculated directly from the pre-catalytic state structure. With the TclForces functionality in NAMD, an in-house TCL (Tool Command Language) script was used to implement the mass-weighted partial tMD simulations. During tMD, the Cα atoms of the protein residues (excluding HNH domain) exhibiting low fluctuations was weakly restrained with a force constant of 0.1 kcal/mol/Å$^2$ to prevent solute drift. Based on previous experience (Zuo et al., *J. Phys. Chem. B* 120, 2145-2154, 2016), a small force constant of 0.25 kcal/mol/Å$^2$ per targeted atoms was adopted, and the simulation length reached up to 100 ns, representing a decreasing rate in RMSD of approximately 0.1 Å per ns. The tMD simulations were performed in NVT ensemble with a time step of 1 fs. The above procedure could ensure a least perturbation on the system resulting from external forces applied by tMD.

Post Targeted Molecular Dynamics Simulations.

At the end of tMD, the RMSD difference reduced to ~0.8 Å, indicating completion of the expected conformational transition. Two trajectory snapshots at ~90 ns of the above parallel tMD (G5, Table 1) were then extracted and subjected to 50-ns equilibration with gradually released restraints on the protein backbone atoms. The final structures were used to seed subsequent unbiased MD simulations (G6, Table 1), in which one Mg$^{2+}$ was introduced at between the HNH active site and the ntDNA scissile phosphate according to the one-metal-ion mechanism. Each run was extended to 800 ns (G6, Table 1). Here, the inventors did not employ the tMD end structures (i.e., at 100 ns) as the start points for Mg$^{2+}$ introduction, given that the modeled target coordinates used in tMD do not necessarily represent a true catalytic state, and importantly, that the Mg$^{2+}$ might assist further conformation change to bridge the distance gap for catalysis as we previously demonstrated (Zuo and Liu, *Sci. Rep.* 5, 2016). This consideration allowed for spontaneous adaptation of the system to the catalytic conformation, thereby eliminating the potential artifacts from tMD. To probe the role of Mg$^{2+}$, the inventors proceeded to perform a set of conventional simulations started from the derived catalytic state, in which the above placed Mg$^{2+}$ was moved from the active center to the bulk solution (G7, Table 1).

Trajectory Analysis Methods.

Details of principal component analysis (PCA), cluster analysis, binding free energy and non-bonded interaction energy calculations and other analyses are presented below.

Principal Component Analysis (PCA).

PCA is a technique for transforming a series of potentially coordinated observations into a set of orthogonal vectors called principal components (PCs) and is widely used to characterize the dominant modes of motion underlying protein dynamics (David and Jacobs, *Methods Mol. Biol.* 1084:193-226, 2014; Amadei et al., *Proteins* 17:412-25, 1993). The calculations of PCs involve two main steps, (i) the calculation of covariance matrix, and (ii) the diagonalization of this matrix. With the goal of comparing the conformational dynamics of HNH domain between different MD simulations, the whole simulation trajectories (G1-G4 and G9, Table 1) were first combined and superimposed to the starting crystal structure using the Cas9 Cα atoms excluding those on the HNH domain. After that, the PCA calculations were performed only on the HNH domain to determine the eigen-vectors and associated eigen-values (referred to collectively as eigen-mode). The eigen-vector with the largest eigen-value corresponds to the lowest mode of motion. The PC analysis was done with the ccptraj module included within the AmberTools16 (Salomon-Ferrer et al., *Wiley Interdiscip. Rev. Comput. Mol. Sci.* 3:198-210, 2013).

HNH Active State Modeling and HNH Pairwise RMSD Computation.

Starting from the pre-catalytic Cas9 structure (PDB code: 5F9R (Jiang et al. *Science* 351:867-871, 2016), the detailed procedure modeling its putative catalytic state of HNH domain from the homologous T4 Endonuclease VII (Endo VII) complexed with a DNA Holliday junction (PDB code: 2QNC (Biertumpfel et al., *Nature* 449:616-U614, 2007) is illustrated in FIG. 11. It should be mentioned that 2QNC represents a catalytically active state where one Mg$^{2+}$ was coordinated at the interface between the enzyme ββα motif and scissile phosphate (see also FIG. 2c-2d), making it the best candidate for active state modeling among the available ββα-metal nuclease structures.

Figures 11A, 11B, 11C, 11D, 11E, 11F:
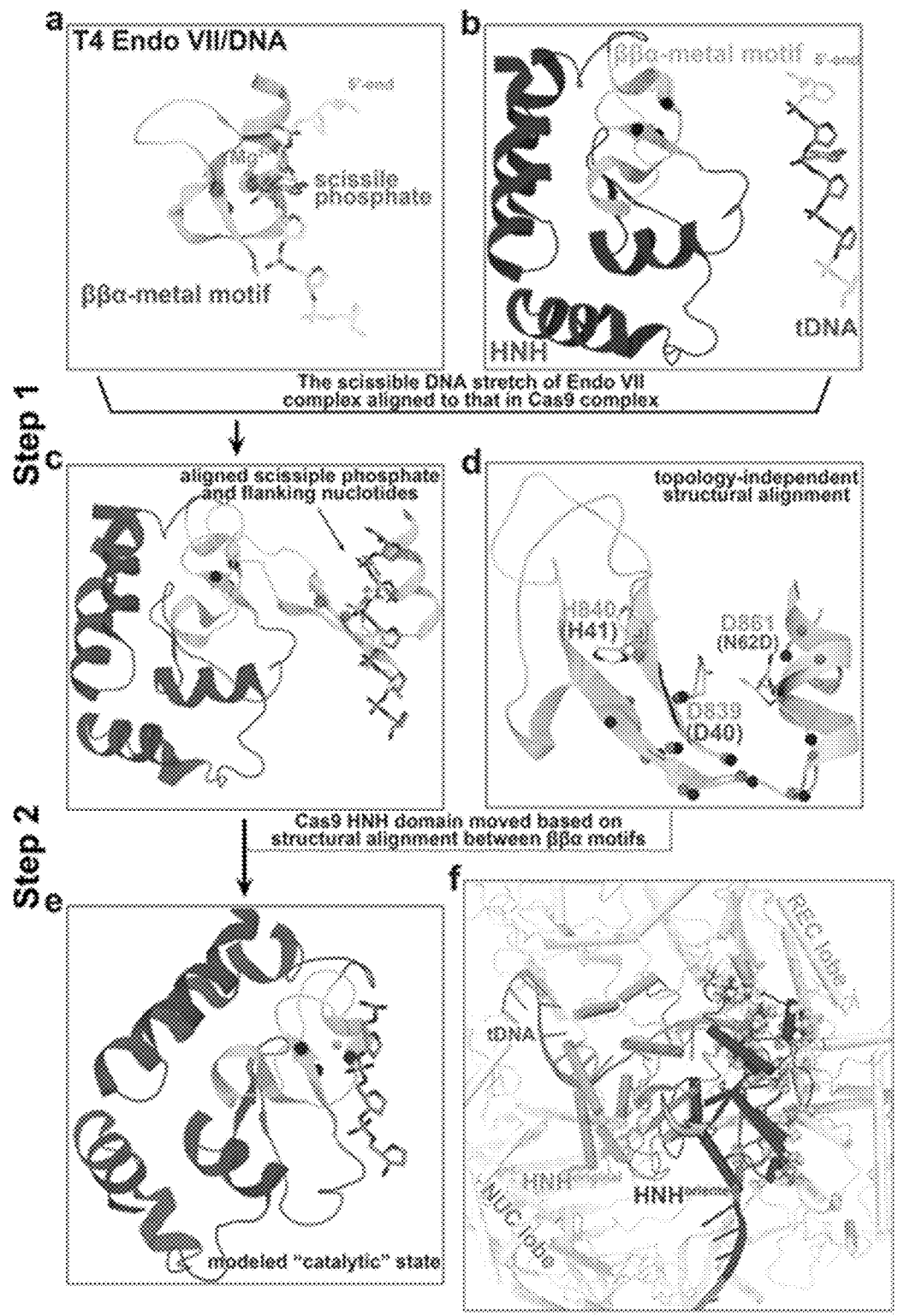
FIGS. 11a-11f. Putative catalytic state of Cas9 HNH domain modeled from T4 Endonuclease VII (Endo VII)/DNA complex (PDB code: 2QNC). (a) T4 Endo VII ββα-metal motif complexed with a DNA substrate. The Cα atoms of the active residues (i.e., Asp40, His840 and Asn62) are rendered as spheres, and the coordinated Mg2+ is depicted as a sphere. (b) Cas9 HNH domain opposite to the target DNA strand (PDB code: 5F9R). The Cα atoms of the putative catalytic residues (i.e., Asp839, His840 and Asp861) are represented as spheres and the HNH domain ββα-metal motif is shown. (c) The scissile phosphate and flanking nucleotides of the DNA substrate in a superimposed onto the corresponding stretch in b alongside the ββα-metal motif. (d) Topology-independent structural alignment between Cas9 and Endo VII ββα-metal motifs (PDB codes: 5F9R and 2QNC) using the CLICK algorithm (Nguyen et al., Nucleic Acids Res. 39, W24-W28, 2011). The Cα RMSD of the equivalent residues (shown as spheres) between the two nucleases is 1.2 Å. The catalytic residues appear to be spatially superimposed well. (e) Cas9 HNH domain oriented toward the target DNA strand based on the transformation matrix obtained from d. (f) Direct "docking" of the HNH domain starting from the pre-catalytic state (PDB code: 5F9R) results in a number of steric clashes with other components in the system. The overlapping heavy atoms are shown as van der Walls spheres, using a distance cutoff of 1.4 Å. The pairwise RMSD for the HNH domain backbone is 25 Å here.

The inventors took three steps to model the HNH active state. In step 1, the scissile phosphate and flanking nucleotides in the T4 Endo VII system (2QNC) was aligned to the corresponding tDNA stretch in the Cas9 complex of the pre-catalytic state (5F9R). In step 2, Cas9 HNH domain was moved toward the tDNA with the transformation matrix calculated from the paired ββα motifs in the two nucleases, resulting in a model of the HNH domain docked at the cleavage site. Notably, the equivalent residues between the above ββα motifs for transformation matrix calculation were determined based on topology-independent structure superposition by the CLICK algorithm (Nguyen et al., *Nucleic Acids Res.* 39:W24-W28, 2011) instead of generally used sequence alignment. The backbone RMSD of HNH domain between the pre-catalytic Cas9 state (5F9R) and the modeled "active" state is 25 Å (FIG. 11f). In step 3, the inventors repeated step 1 and step 2, replacing the crystal structure (5F9R) with snapshot structures from the sets of long cMD trajectories (G1 and G2, Table 1). A modeled "active" state was obtained for every snapshot of the simulations. The inventors calculated RMSD between the snapshot structure and its corresponding "active" state and used it as a metric to evaluate how close the snapshot conformation to its putative active state.

Details of Generating tMD-Derived Catalytic State.

The inventors employed the targeted molecular dynamics (tMD) method to drive Cas9 conformational transition. The target structures for tMD were built by reference to the catalytically active T4 Endo VII system above (FIG. 11). To minimize the potential artificial effect by tMD, two snapshots were extracted from the sets of long cMD trajectories (G1 and G2, Table 1) as the starting structures that show most proximity to the their respective modeled "active" states in terms of HNH domain conformation (FIG. 11). The backbone RMSD differences for the HNH domain from the target structures are about 10 Å, which are remarkably reduced as compared with that of 25 Å if using the pre-catalytic crystal structure (5F9R) as the starting point. Accordingly, the tMD stating points were much closer to the corresponding end points in the subspace defined by the first two principal components with regard to the crystal structure (FIG. 1d). Docking of the HNH domain toward the putative catalytic state inevitably brings about numerous steric clashes with the other components in the complex system (FIG. 11f), indicating considerable conformational rearrangements in Cas9 must be implicated during the pre-catalytic to catalytic state transition. The inventors note that the trajectory snapshots from aMD were not employed, albeit further approach to the target conformations with a minimum RMSD difference of ~5 Å, as it appears that the enhanced sampling via aMD also accompanies an appreciable distortion regarding the internal conformation of HNH domain (FIG. 10 and Table 2). During tMD, the Cα atoms of the protein residues (excluding HNH domain) exhibiting low fluctuations were weakly restrained with a force constant of 0.1 kcal/mol/Å$^2$ to prevent solute global drift. The guiding forces were exerted only on the HNH domain backbone atoms with a force constant of 0.5 kcal/mol/Å$^2$, and the simulation time was set to 100 ns (G5, Table 1), representing a RMSD decreasing rate of approximately 0.1 Å/ns.

At the end of tMD, the RMSD between the initial and target coordinates declined to ~0.8 Å, indicating completion of the anticipated conformation change. The inventors selected two structure snapshots that are at near the end of tMD for subsequent cMD (G6, Table 1), in which one Mg$^{2+}$ was introduced at the interface between the HNH domain and tDNA in the framework of the one-metal-ion mechanism (FIG. 2d)(Yang, Q. Rev. Biophys. 44:1-93, 2011; Yang, Nat. Struct. Mol. Biol. 15:1228-31, 2008). Here, the inventors did not employ the tMD end structures (i.e., at 100 ns) as the start points for Mg$^{2+}$ introduction, given that the modeled target coordinates used in tMD do not necessarily represent a true catalytic state, and importantly, that the Mg$^{2+}$ may assist further conformation change to bridge the distance gap for catalysis as previously demonstrated with the RuvC domain (Zuo and Liu, Sci. Rep. 5, 2016). This consideration allowed for spontaneous adaptation of the system to the catalytic conformation. The deliberate building procedures could ensure least perturbation on the system and hence eliminate potential artificial effects by the tMD that is readily subjected to question. After sufficient equilibration, the inventors obtained a reasonable catalytic conformation, featuring stable Mg$^{2+}$-involved coordination configuration (FIG. 2b) that matches well with that observed in the T4 Endo VII system (FIG. 2c).

Details of Generating cMD$^{ens}$-Derived Catalytic State.

The above tMD-based strategy to capture the catalytic state in essence is dependent on a modeled putative "target" state. One may question the reliability of the derived state and associated results, though the model was treated with careful considerations. To eliminate these concerns, the inventors developed an ensemble sampling-based scheme targeting the active state forward. The basic idea is as follows: (i) pre-define an a priori metric (or multiple if necessary) like distance, angle and RMSD; (ii) use this metric to track conformational transition and screen a structure most approximate to expected target state; (iii) perform ensemble conventional MD simulations (cMD$^{ens}$) starting from the above extracted structure; (iv) screen another closest structure snapshot from previous cMD$^{ens}$ and initiate a new cycle of ensemble simulations. Ideally, the inventors get closer to or even hit the target conformation through several or more cycles, depending on the energetic barrier height between the initial and target states and the sampling length accessible to each independent run.

The inventors used the geometric mean of the distances of +4P (the scissile phosphate) to the two active residues His840 and Asp861 ($\sqrt{d_{+4P-H840}*d_{+4P-D61}}$) as a metric to monitor the HNH domain conformational change: the smaller this value, the closer to the target active state (FIGS. 4a and 4b). From the sets of long cMD trajectories (G1 and G2, Table 1), a structure bearing a minimum value of ~9 Å was extracted as the starting point for ensemble simulations (FIG. 3a), where one Mg$^{2+}$ was placed around the reaction center as done for the post tMD simulations. In each cycle, a total of 10 independent runs were carried out and each run lasted 500 ns (G8.1-G8.4, Table 1). Through four cycles, the above geometric mean got sable at ~6 Å (FIG. 3a), which is comparable to that observed for the tMD-derived catalytic state (FIG. 4a). Accordingly, the RMSD of the reaction interface from the tMD-derived catalytic state declined from initial ~3 Å to ~1 Å (FIG. 4b). Moreover, the Mg$^{2+}$-involved coordination composition and configuration here (FIG. 2b) are essentially the same to those derived from tMD (FIG. 2a), except that Tyr823 was engaged to Asp839 via an intercalated water molecule, again confirming the structural role of Tyr823 around the reaction center. These observations thus demonstrated formation of the cMD$^{ens}$-derived catalytic state.

Cluster Analysis.

The simulation structures used for visualization and comparison were determined through the cluster analysis with the package VMD (version 1.9.2)(Humphrey et al., J. Mol. Graph. Model. 14:33-38, 1996). Following previous experience with the same system (Zuo and Liu, Sci. Rep. 5, 2016) the reaction interface atoms were selected for calculations, involving the heavy atoms of the three active residues, Asp839, His840 and Asp861, the Cα atoms of the remaining residues on the HNH ββα motif, the backbone of the scissile stretch on the tDNA (+3P to +5P), and the coordinated Mg$^{2+}$ between them. By varying the RMSD cutoff (0.6-1.0 Å here), four groups were obtained in which the first two account for >80% of total population. The structure(s) closest to the centroid of the largest ensemble were extracted for analysis.

Binding Free Energy Calculation and Per-Residue Energy Decomposition.

The end-point Molecular Mechanics-Generalized Born Surface Area (MM-GBSA) approach (Hou et al., *J. Chem. Inf. Model.* 51:69-82, 2011) was employed to estimate per-residue energetic contribution to $Mg^{2+}$ binding and the difference in the affinities of the tDNA to Cas9 with and without $Mg^{2+}$ bound at the reaction interface. Compared to the alternative Molecular Mechanics-Poisson Boltzmann Surface Area (MM-PBSA), MM-GBSA is computationally more efficient and has shown to give comparable or even better accuracy (Hou et al., *J. Chem. Inf. Model.* 51:69-82, 2011; Zuo et al., *J. Phys. Chem. B* 120:2145-54, 2016). All the MM-GBSA calculations were performed with the program MMPBSA.py in AmberTools16 (Miller et al., *J. Chem. Theory Comput.* 8:3314-21, 2012). The entropic contribution was not taken into account here, as omission of this term does not qualitatively affect the results (Hou et al., *J. Chem. Inf. Model.* 51:69-82, 2011; Zuo et al., *J. Phys. Chem. B* 120:2145-54, 2016). The last 400 ns of each set of simulation trajectories were used for calculations, with 50-ps intervals. Specially, in the case of $Mg^{2+}$ binding free energy calculation, the three water molecules closest to the coordinated $Mg^{2+}$ in each trajectory snapshot were retained and considered as part of the Cas9-sgRNA/tDNA "receptor".

Non-Bonded Interaction Energy Calculation.

The non-bonded interaction energies of the HNH $\beta\beta\alpha$ motif with the scissile phosphate and flanking nucleotides (+3P to +5P) were calculated by the software NAMD (version 2.12)(Phillips et al., *J. Comput. Chem.* 26:1781-1802, 2005), employing the same structural ensemble as mentioned above. The truncation cutoff was set to 10 Å, consistent with that used in MD simulations.

Figures 15A, 15B:
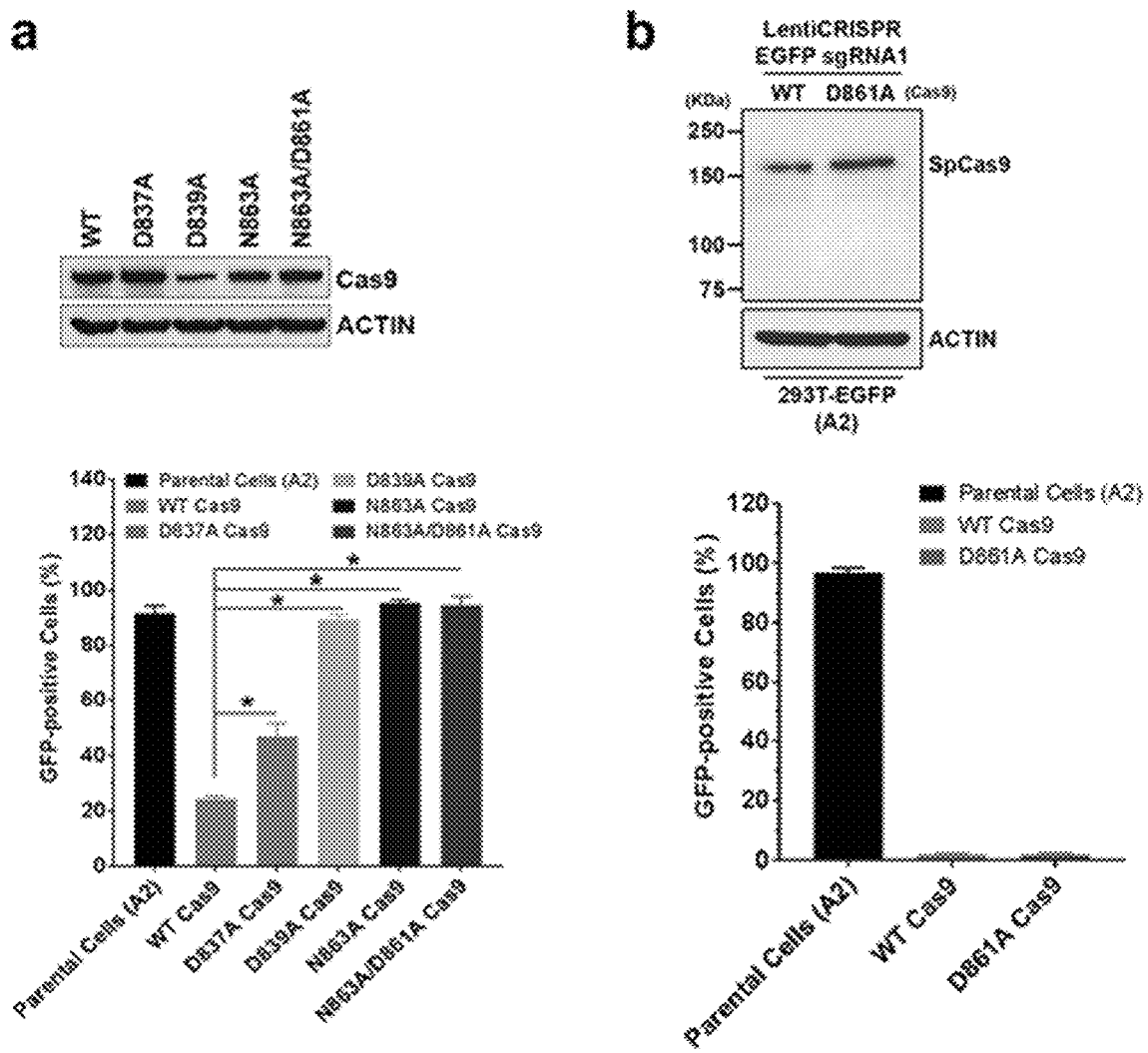
FIG. 15a-15b. Illustrates an active state of the Cas9 HNH domain identified by computer modeling and simulations can be responsible for the tDNA cleavage. Site-directed mutagenesis experiments with four single mutations (D837A, D839A, D861A, and N863A) plus one double mutation (D861A/N863A) suggest that D839 and N863 are residues involved in Cas9 activity by directly coordinating the catalytic $Mg^{2+}$ at the interface between the HNH domain and tDNA, validating the newly identified active state.

The inventors have identified two states, the pseudo active state and the active state, using computational techniques. These two states have similar global conformations. The major distinction lies in the local conformation involving the residues N863 and D861. The active state of the Cas9 HNH domain identified by computer modeling and simulations is responsible for the tDNA cleavage. The inventors have performed site-directed mutagenesis experiments to validate this newly identified active state. Four single mutations (D837A, D839A, D861A, and N863A) plus one double mutation (D861A/N863A) was performed (FIG. 15). Remarkably, the combined experimental and computational data suggest that D839 and N863 are the essential residues for Cas9 activity by directly coordinating the catalytic $Mg^{2+}$ at the interface between the HNH domain and tDNA, validating the newly identified active state.

Both the pseudo-active and active states exist during the Cas9 conformational transition and the relevant structural information could be exploited for rational design of enhanced specificity Cas9 variants. Further comparison of the two conformational states reveal that the major structural differences lie in the interactions of the HNH domain with the REC1 domain. Collectively,—the data have identified two new interacting pairs, viz., Glu371 with Lys866 and Asp406 with Arg864, It is contemplated that alanine substitution at the sites can be beneficial and result in improved Cas9 specificity.

The initial model for the active Cas9 complex was constructed by replacing the $\alpha$ segment of the $\beta\beta\alpha$-Me motif in the optimized catalytic Cas9 complex with the corresponding part in the Mg2+-bound apo-Cas9 structure (PDB code: 4CMP). The catalytic Cas9 complex structure was taken from the above production simulation, as described in [137], near 100 ns (i.e., about half of the simulation time), and the Mg2+-bound apo-Cas9 structure from the simulation trajectory was selected based on the observation of reasonable bonding with the connecting residues and minimal steric clashes after replacement of the $\alpha$ segment. After thorough energy minimization, the structural model was subjected to multi-stage equilibration: an initial 20-ns relaxation of the $\alpha$ segment and surrounding residues, an another 20-ns equilibration with the inter-atomic distances within the metal center retrained relative to the T4 Endo VII system, followed by a 20-ns equilibration with the restraints gradually released. Subsequently, two independent replicas were performed (250 ns/run) under the same simulation conditions set for the pseudo-active system above.

Ten Cas9 variants were designed and synthesized to test its activity and specificity. (Table 5). The mutation designed in each variant followed the combination of five rationales, including (1) weakening Cas9 binding affinity with tDNA; (2) weakening Cas9 binding affinity with ntDNA; (3) weakening Cas9 binidng affinity with sgRNA; (4) raising threshold energy for Cas9 HNH domain conformational activation; (5) destablizing the formation of Cas9 HNH domain active conformation.

Figures 16A, 16B, 16C:
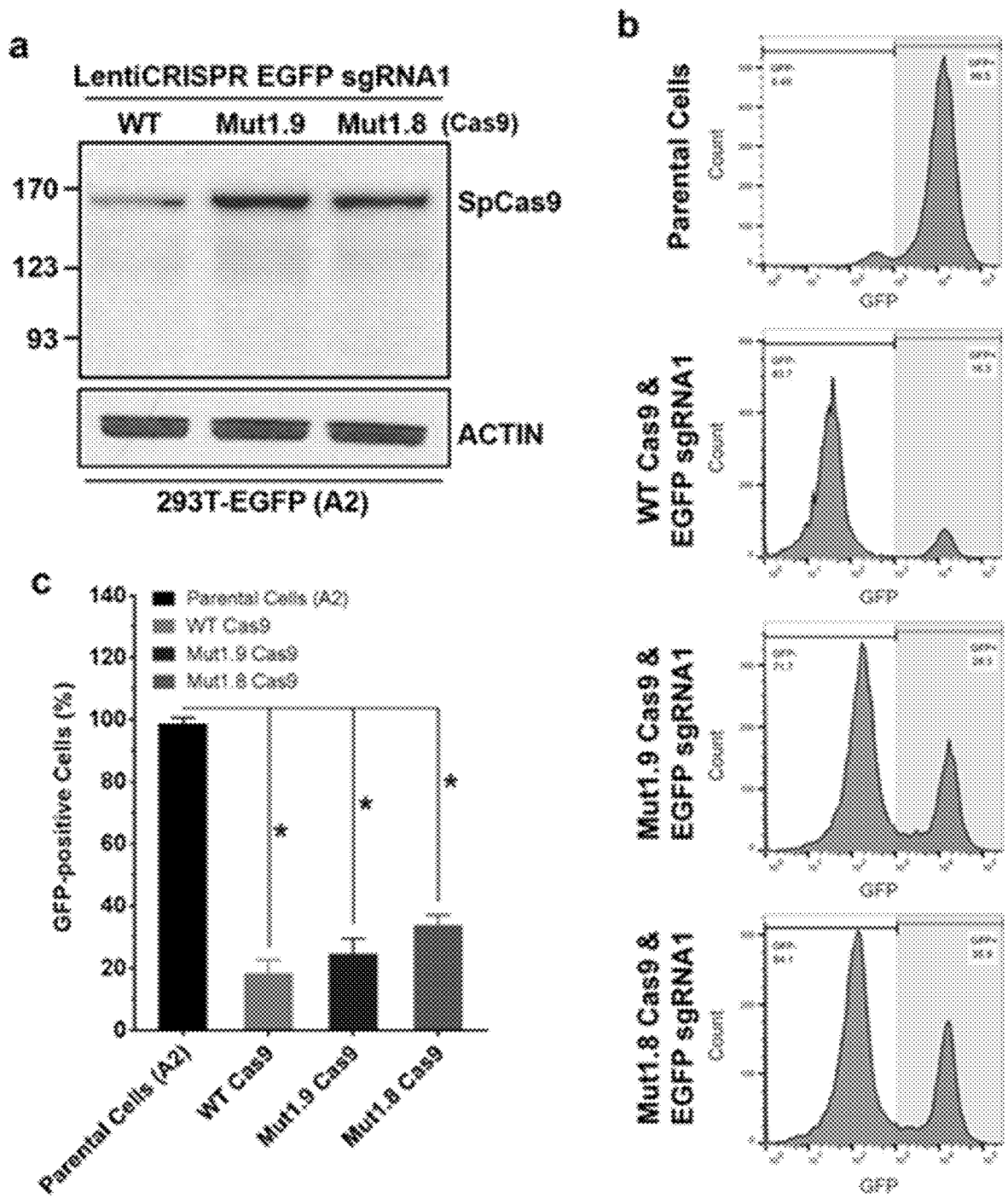
FIG. 16a-16c. The gene-editing activity of two tetra-mutant variants of Cas9. (a) The expression of different Cas9 variants in HEK293T-EGFP cells. WT: wild-type. Mut1.8: N588A/R765A/D835A/K1246A. Mut1.9: N14A/R447A/R765A/S845D. (b) The representative histograms of flow cytometry analysis of EGFP-positive cells in the HEK293T-EGFP cells expressing the indicated Cas9 variants and EGFP gene-targeting sgRNA. (c). The quantitative data of EGFP-positive cells in each sample. Similar to the wild-type Cas9, the Mut1.8 and Mut1.9 Cas9 variants were highly active in gene editing that led to the loss of EGFP expression in the cells. *$P<0.05$ (Student's t-test).

Two variants include mutations designed on all of the five rationales. These two mutants are N588A/R765A/D835A/K1246A (Mut1.8) and N14A/R447A/R765A/S845D (Mut1.9) (Table 5, FIG. 16a-16c). The gene-editing activities and specificity assays of these two tetramutant variants of Cas9 (FIG. 16a-16c) were performed. Using HEK293T-EGFP cells, the above two tetramutants exhibit similar protein expression level and comparable gene-editing efficiency compared to the wild type Cas9 (FIG. 16a-16c), indicating these two designed variants do not significantly alter the on-target activity.

TABLE 2

| PDB code | apo-Cas9 | | | Cas9-sgRNA | | | Cas9-sgRNA-DNA | | |
|---|---|---|---|---|---|---|---|---|---|
| | 4CMP_A | 4CMP_B | 4CMQ_A | 4ZT0_A | 4ZT0_C | 4ZT9_A | 4OO8_A | 4UN3_B | 5F9R_B |
| a | Pairwise RMSDs for the Cα atoms of HNH domain† among different Cas9 crystal structures [mean = 1.4 (0.6) Å] | | | | | | | | |
| 4CMP_A* | | 0.5 | 0.5 | 1.9 | 2.4 | 1.8 | 1.8 | 1.8 | 1.8 |
| 4CMP_B | 0.5 | | 0.5 | 1.9 | 2.5 | 1.9 | 1.9 | 1.9 | 1.9 |
| 4CMQ_A | 0.5 | 0.5 | | 1.7 | 2.3 | 1.7 | 1.7 | 1.7 | 1.7 |
| 4ZT0_A | 1.9 | 1.9 | 1.7 | | 1.5 | 0.6 | 0.7 | 0.7 | 0.8 |
| 4ZT0_C | 2.4 | 2.5 | 2.3 | 1.5 | | 1.6 | 1.6 | 1.5 | 1.6 |
| 4ZT9_A | 1.8 | 1.9 | 1.7 | 0.6 | 1.6 | | 0.8 | 0.8 | 0.9 |
| 4OO8_A | 1.8 | 1.9 | 1.7 | 0.7 | 1.6 | 0.8 | | 0.5 | 0.7 |
| 4UN3_B | 1.8 | 1.9 | 1.7 | 0.7 | 1.5 | 0.8 | 0.5 | | 0.7 |
| 5F9R_B | 1.8 | 1.9 | 1.7 | 0.8 | 1.6 | 0.9 | 0.7 | 0.7 | |

TABLE 2-continued

|  | apo-Cas9 | | | Cas9-sgRNA | | | Cas9-sgRNA-DNA | | |
|---|---|---|---|---|---|---|---|---|---|
| PDB code | 4CMP_A | 4CMP_B | 4CMQ_A | 4ZT0_A | 4ZT0_C | 4ZT9_A | 4OO8_A | 4UN3_B | 5F9R_B |
| b \| Pairwise RMSDs for the Cα atoms of HNH ββα fold‡ among different Cas9 crystal structures [mean = 1.4 (0.7) Å] | | | | | | | | | |
| 4CMP_A |  | 0.3 | 0.3 | 2.1 | 2.2 | 2.0 | 2.1 | 2.0 | 2.0 |
| 4CMP_B | 0.3 |  | 0.4 | 2.2 | 2.3 | 2.1 | 2.2 | 2.1 | 2.1 |
| 4CMQ_A | 0.3 | 0.4 |  | 2.1 | 2.1 | 1.9 | 2.0 | 2.0 | 2.0 |
| 4ZT0_A | 2.1 | 2.2 | 2.1 |  | 0.7 | 0.3 | 1.0 | 1.0 | 1.1 |
| 4ZT0_C | 2.2 | 2.3 | 2.1 | 0.7 |  | 0.8 | 0.7 | 0.8 | 0.8 |
| 4ZT9_A | 2.0 | 2.1 | 1.9 | 0.3 | 0.8 |  | 1.0 | 1.0 | 1.0 |
| 4OO8_A | 2.1 | 2.2 | 2.0 | 1.0 | 0.7 | 1.0 |  | 0.4 | 0.5 |
| 4UN3_B | 2.0 | 2.1 | 2.0 | 1.0 | 0.8 | 1.0 | 0.4 |  | 0.4 |
| 5F9R_B | 2.0 | 2.1 | 2.0 | 1.1 | 0.8 | 1.0 | 0.5 | 0.4 |  |

†Residues 781 to 905;
‡Residues 837 to 867;
*Chain identifier present in the PDB file.

TABLE 3

Average pairwise Cα RMSDs of tMD-derived and cMD$^{ens}$-derived catalytic Cas9 aggregates relative to the crystal structure (upper) and between the two structural ensembles (lower) [Å]*

|  | ALL† | RuvC‡ | Topo | CTD | HNH | REC1 | REC2 | REC3 |
|---|---|---|---|---|---|---|---|---|
| Relative to the crystal structure [PDB code: 5F9R]¶ | | | | | | | | |
| tMD-derived catalytic state | 5.6 (0.2) | 3.0 (0.2) | 3.8 (0.6) | 7.2 (0.7) | 10.6 (0.3) | 4.0 (0.4) | 7.0 (0.4) | 3.4 (0.3) |
| cMD$^{ens}$-derived catalytic state | 5.7 (0.2) | 2.7 (0.3) | 3.0 (0.5) | 6.8 (0.8) | 11.5 (0.6) | 3.2 (0.5) | 7.9 (0.7) | 2.9 (0.3) |
| Relative to the crystal structure [PDB code: 5F9R]§ | | | | | | | | |
| tMD-derived catalytic state | 5.6 (0.2) | 1.7 (0.1) | 2.6 (0.5) | 3.6 (0.5) | 1.3 (0.2) | 1.6 (0.1) | 1.9 (0.1) | 2.5 (0.1) |
| cMD$^{ens}$-derived catalytic state | 5.7 (0.2) | 1.7 (0.2) | 2.3 (0.3) | 3.5 (0.4) | 1.4 (0.3) | 1.5 (0.1) | 1.9 (0.2) | 2.2 (0.2) |

| ALL | RuvC | Topo | CTD | HNH | REC1 | REC2 | REC3 |
|---|---|---|---|---|---|---|---|
| Between the two different derived catalytic states¶ | | | | | | | |
| 2.6 (0.1) | 1.8 (0.2) | 1.8 (0.4) | 3.6 (0.3) | 2.5 (0.5) | 2.0 (0.2) | 2.0 (0.3) | 2.4 (0.1) |
| Between the two different derived catalytic states§ | | | | | | | |
| 2.6 (0.1) | 1.2 (0.1) | 1.0 (0.2) | 3.1 (0.1) | 1.2 (0.4) | 1.2 (0.1) | 1.1 (0.2) | 1.9 (0.1) |

*tMD, targeted MD; cMD$^{ens}$, ensemble conventional MD. See Table 1 in main text. An aggregate of 50 most populated structures were extracted for calculations based on cluster analysis (Supplementary Text)
†The whole protein
‡Residues 1047-1071 and 1016-1031 excluded. Due to the absence of 5'-end ntDNA⁴, this local binding groove exhibits remarkable opening and closing mobility.
¶Best-fit to the Cα atoms of the whole reference protein prior to RMSD calculations
§Best-fit to the Cα atoms of individual protein domains prior to RMSD calculations

TABLE 4

Summary of the interacting pairs between Cas9 HNH domain and other components in the complex system from biased (tMD) and unbiased ensemble (cMD$^{ens}$) simulations and comparison with the starting pre-catalytic structure

| Cas9 domain | HNH domain* | Interaction pattern§ | Catalytic state [tMD]† (occurrence %) | Pre-catalytic state [5F9R]‡ | Catalytic state [cMD$^{ens}$]¶ | Suggested substitution# |
|---|---|---|---|---|---|---|
| REC3 | Glu584 | Lys775 | Salt bridge/H-bond | 19 | — | ✓ |  |
|  | Asp585 |  |  | 27 | — | — |  |
|  | Asp585 | Arg778 | Salt bridge/H-bond | 16 | — | ✓ |  |
|  | Lys558 | Glu779 | Salt bridge/H-bond | 17 | — | ✓ | Arg586Ala |
|  | Arg586 |  |  | 48 | — | ✓ | Glu779Ala |

TABLE 4-continued

Summary of the interacting pairs between Cas9 HNH domain and other components in the complex system from biased (tMD) and unbiased ensemble (cMD$^{ens}$) simulations and comparison with the starting pre-catalytic structure

| Cas9 domain | HNH domain* | Interaction pattern§ | Catalytic state [tMD]† (occurrence %) | Pre-catalytic state [5F9R]‡ | Catalytic state [cMD$^{ens}$]¶ | Suggested substitution# |
|---|---|---|---|---|---|---|
| REC2 | Asp261 | Gln805 | H-bond | 7 | — | ✓ | |
| | Lys263 | | | 16 | — | ✓ | |
| | Lys234 | Asp829 | Salt bridge/H-bond | 15 | — | ✓ | |
| | Asn235 | | H-bond | 13 | — | ✓ | |
| | Glu223 | Arg832 | Salt bridge/H-bond | 91 | — | ✓ | Glu223Ala |
| | | Arg859 | Salt bridge/H-bond | 18 | — | ✓ | Arg859Ala |
| | Thr249 | Asn831 | H-bond | 27 | — | ✓ | |
| | Asn251 | | | 46 | — | ✓ | |
| | Gly247 | Ser834 | H-bond | 44 | — | ✓ | |
| | Thr249 | | | 16 | — | ✓ | |
| | Ser217 | Asp835 | H-bond | 43 | — | ✓ | Asp835Ala |
| | Lys218 | | | 55 | — | ✓ | |
| | Ser219 | | | 99 | — | ✓ | |
| BH | Thr58 | Lys848 | H-bond | 57 | — | ✓ | |
| | Glu60 | Lys848 | Salt bridge/H-bond | 51 | — | ✓ | |
| | | Gln844 | H-bond | 20 | — | ✓ | |
| REC1 | Glu370 | Lys862 | Salt bridge/H-bond | 61 | — | ✓ | Glu370Ala |
| | Glu396 | | | 68 | — | ✓ | Glu396Ala |
| | Glu370 | Lys866 | Salt bridge/H-bond | 25 | — | ✓ | Lys866Ala |
| | Glu371 | | | 18 | — | ✓ | |
| tDNA | DT23 | Arg765 | Salt bridge/H-bond | 100 | ✓ | ✓ | |
| | DA24 | | | 16 | ✓ | ✓ | |
| | DT25 | Asn767 | H-bond | 92 | ✓ | ✓ | Asn767Ala |
| | DG13 | Ser845 | H-bond | 93 | — | ✓ | Ser845Asp |
| sgRNA | RG2 | Arg765 | Salt bridge/H-bond | 99 | — | ✓ | Arg765Ala |
| | RA9 | Arg780 | Salt bridge/H-bond | 100 | ✓ | ✓ | Arg780Ala |
| | | Arg783 | | 72 | — | ✓ | Arg783Ala |
| | RA8 | Asn803 | H-bond | 94 | — | ✓ | Asn803Ala |
| | | Gln807 | | 37 | — | ✓ | |
| | RA9 | Tyr812 | H-bond | 97 | — | ✓ | Tyr812Ala |
| | RA12 | Lys848 | Salt bridge/H-bond | 89 | — | ✓ | |
| | R13 | | | 81 | — | ✓ | |
| | RG11 | Arg895 | Salt bridge/H-bond | 99 | — | ✓ | Arg895Ala |

The residues whose alanine substitution was experimentally shown to enhance Cas9 specificity are highlighted (see FIG. 7c). The promising candidate residues for further testing, determined based on our study, are in red boldface.
*Part of HNH domain flanking link regions (L1&L2) included into statistics
§Salt bridge interaction is defined as the distance between the nitrogen and oxygen atoms is less than 4 Å; A hydrogen bond (H-bond) is defined as the distance between the donor and receptor atoms is less than 3.5 Å and the angle formed by the donor, hydrogen and acceptor atoms is less than 35° from 180°.
†Post targeted MD (tMD)-derived interactions (G6 in Table 1).
‡Presence (✓) or not (—) in the initial pre-catalytic crystal structure (PDB code: 5F9R) Presence (✓) or not (—) in the ensemble conventional MD (cMD$^{ens}$)-derived catalytic state
Suggested amino acid mutations for further specificity improvement

TABLE 5

Rational Design of spCas9 Variants with Potential Improved Specifity

| Index | Version | Combination Substition | Rationale* |
|---|---|---|---|
| 1 | HF-spCas9 (v1.0) | K526A/N588A/1R765A/N767A | R1 + R3 + R4 |
| 2 | HF-spCas9 (v1.1) | N588A/K929A/H930A/Y1013A | R1 + R3 + R4 |
| 3 | HF-spCas9 (v1.2) | R447A/K526A/K929A | R1 + R3 + R4 |
| 4 | HF-spCas9 (v1.3) | N588A/N767A/Y1013A/K866A | R1 + R3 + R4 + R5 |
| 5 | HF-spCas9 (v1.4) | N588A/N767A/Y1013A/S845D | R1 + R3 + R4 + R5 |
| 6 | HF-spCas9 (v1.5) | K268A/K526A/N588A/N767A | R1 + R3 + R4 |
| 7 | HF-spCas9 (v1.6) | N14A/K526A/K866A/K1246A | R1 + R2 + R5 |
| 8 | HF-spCas9 (v1.7) | N14A/1R447A/Y1013A/K1246A | R1 + R2 + R3 |
| 9 | HF-spCas9 (v1.8) | N588A/1R765A/D835A/K1246A | R1 + R2 + R3 + R4 + R5 |
| 10 | HF-spCas9 (v1.9) | N14A/R447A/R765A/S845D | R1 + R2 + R3 + R4 + R5 |

*R1: weakening binding affinity with tDNA
R2: weakening binding affinity with ntDNA
R3: weakening binding affinity with sgRNA
R4: rasing threshold enegy for Cas9 HNH domain conformational activation
R5: destabilizing the formation of Cas9 HNH domain active conformation

The invention claimed is:

1. A composition comprising a modified Cas9 protein, wherein the modified Cas9 protein comprises at least three or four modifications to the amino acid sequence corresponding to SEQ ID NO:1, the modifications comprising one or more of N588A/R765A/N767A; N588A/Q695A/R765A/N767A; N588A/N692A/R765A/N767A; N588A/N692A/R765A/R925A; N588A/N692A/N767A/R925A; N692A/R765A/N767A/R925A; Q695A/R765A/N767A/R925A; N588A/N692A/R765A/K929A; N588A/N692A/N767A/K929A; N692A/R765A/N767A/K929A; Q695A/R765A/N767A/K929A; N497A/Q695A/R765A/N767A; K526A/K528A/N497A/Q926A; K526A/K528A/K929A; K526A/R765A/N767A/Y1013A; K528A/R765A/N767A/Y1013A; K526A/R765A/N767A/Q926A; N497A/K526A/R765A/N767A; N497A/K528A/R765A/N767A; N497A/K526A/R765A/Q926A; N497A/K528A/R765A/Q926A; N588A/R765A/N767A/S845D; N588A/R765A/N767A/R832A; N588A/R765A/N767A/K862A; N588A/R765A/N767A/K866A; N588A/R765A/N767A/R859A; N588A/R765A/N767A/Q844A; N588A/R765A/N767A/K810A; N588A/R765A/N767A/K848A; N588A/R765A/N767A/E370A; N588A/R765A/N767A/E223A; N497A/N692A/K1031A/S845D; N497A/N692A/K1031A/R832A; N497A/N692A/K1031A/K862A; N497A/N692A/K1031A/K866A; N497A/N692A/K1031A/R859A; N497A/N692A/K1031A/Q844A; N497A/N692A/K1031A/K810A; N497A/N692A/K1031A/K848A; N497A/N692A/K1031A/E370A; N497A/N692A/K1031A/E223A; N497A/N695A/K1031A/S845D; N497A/N695A/K1031A/R832A; N497A/N695A/K1031A/K862A; N497A/N695A/K1031A/K866A; N497A/N695A/K1031A/R859A; N497A/N695A/K1031A/Q844A; N497A/N695A/K1031A/K810A; N497A/N695A/K1031A/K848A; N497A/N695A/K1031A/E370A; N497A/N695A/K1031A/E223A; K526A/N695A/K1031A/S845D; K526A/N695A/K1031A/R832A; K526A/N695A/K1031A/K862A; K526A/N695A/K1031A/K866A; K526A/N695A/K1031A/R859A; K526A/N695A/K1031A/Q844A; K526A/N695A/K1031A/K810A; K526A/N695A/K1031A/K848A; K526A/N695A/K1031A/E370A; K526A/N695A/K1031A/E223A; K528A/N695A/K1031A/S845D; K528A/N695A/K1031A/R832A; K528A/N695A/K1031A/K862A; K528A/N695A/K1031A/K866A; K528A/N695A/K1031A/R859A; K528A/N695A/K1031A/Q844A; K528A/N695A/K1031A/K810A; K528A/N695A/K1031A/K848A; K528A/N695A/K1031A/E370A; K528A/N695A/K1031A/E223A; N692A/R765A/Y1013A; N692A/R765A/S845D/Y1013A; N692A/R765A/R832A/Y1013A; N692A/R765A/K862A/Y1013A; N692A/R765A/K866A/Y1013A; N692A/R765A/R859A/Y1013A; N692A/R765A/Q844A/Y1013A; N692A/R765A/K810A/Y1013A; N692A/R765A/K848A/Y1013A; N692A/R765A/E370A/Y1013A; N692A/R765A/E223A/Y1013A; N692A/R765A/Y1013A; N692A/Q695A/K810A/Y1013A; N692A/Q695A/K848A/Y1013A; K526A/K528A/Y1013A; K526A/K528A/K268A/Y1013A; R447A/K526A/K528A/Y1013A; R765A/K929A/H930A; R765A/K929A/S845D/Y1013A; R765A/K929A/R832A/Y1013A; R765A/K929A/K862A/Y1013A; R765A/K929A/K866A/Y1013A; R765A/K929A/R859A/Y1013A; R765A/K929A/Q844A/Y1013A; R765A/K929A/K810A/Y1013A; R765A/K929A/K848A/Y1013A; R765A/K929A/E370A/Y1013A; R765A/K929A/E223A/Y1013A; R765A/Q926A/K929A/H930A; R447A/K500A/R661A; K500A/N695A/K929A/S845D; K500A/N695A/K929A/R832A; K500A/N695A/K929A/K862A; K500A/N695A/K929A/K866A; K500A/N695A/K929A/R859A; K500A/N695A/K929A/Q844A; K500A/N695A/K929A/K810A; K500A/N695A/K929A/K848A; K500A/N695A/K929A/E370A; K500A/N695A/K929A/E223A; R765A/R925/Q926A; R765A/R925/Q926/Y1013A; N14A/K961A/K968A; N14A/K961A/K968A/S845D; N14A/K961A/K968A/K848A; R447A/R765A/Y1013A; K526A/N588A/R765A/N767A; N588A/K929A/H930A/Y1013A; R447A/

K526A/K929A; N588A/N767A/Y1013A/K866A; N588A/ N767A/Y1013A/S845D; K268A/K526A/N588A/N767A; N14A/K526A/K866A/K1246A; N14A/R447A/Y1013A/ K1246A; N588A/R765A/D835A/K1246A; N14A/R447A/ R765A/S845D; K1244A/K1246A/K848A; K1244A/ K1246A/K810A; K1244A/K1246A/R832A; K1244A/ K1246A/K862A; K1244A/K1246A/K866A; K1244A/ K1246A/K859A; K1244A/K1246A/E370A; K1244A/ K1246A/E223A; K1244A/K1246A/S845D; K1244A/ K1246A/Q844A; K1244A/K1246A/0844A/K1031A; K1244A/K1246A/Q844A/Y1013A; K1244A/K1246A/ Q844A/N695A; K1244A/K1246A/Q844A/N692A; K1244A/K1246A/Q844A/N588A; K1244A/K1246A/ Q844A/N767A; K1244A/K1246A/Q844A/Q926A; K268A/ R447A/Y450A/K1031A; K268A/R447A/Y450A/Y1013A; K268A/R447A/Y450A/N695A; K268A/R447A/Y450A/ N692A; K268A/R447A/Y450A/N588A; K268A/R447A/ Y450A/N767A; K268A/R447A/Y450A/Q926A; N14A/ K268A/R447A/Y450A; N14A/Y450A/K526A/K528A; N14A/Y450A/R765A/S845D); N14A/Y450A/R765A/ R832A; N14A/Y450A/R765A/K862A; N14A/Y450A/ R765A/K866A; N14A/Y450A/R765A/R859A; N14A/ Y450A/R765A/Q844A; N14A/Y450A/R765A/K810A; N14A/Y450A/R765A/K848A; N14A/Y450A/R765A/ E370A; N14A/Y450A/R765A/E223A; R447A/Y450A/ R765A/S845D; R447A/Y450A/R765A/R832A; R447A/ Y450A/R765A/K862A; R447A/Y450A/R765A/K866A; R447A/Y450A/R765A/R859A; R447A/Y450A/R765A/ Q844A; R447A/Y450A/R765A/K810A; R447A/Y450A/ R765A/K848A; R447A/Y450A/R765A/E370A; R447A/ Y450A/R765A/E223A; K268A/R447A/R765A/S845D; K268A/R447A/R765A/R832A; K268A/R447A/R765A/ K862A; K268A/R447A/R765A/K866A; K268A/R447A/ R765A/R859A; K268A/R447A/R765A/Q844A; K268A/ R447A/R765A/K810A; K268A/R447A/R765A/K848A; K268A/R447A/R765A/E370A; K268A/R447A/R765A/ E223A; Q805A/D829A/N831A/D835A; R765A/D829A/ D835A/Y1013A; R918A/D829A/D835A/Y1013A; R895A/ D829A/D835A/Y1013A; K500A/D829A/D835A/Y1013A; K929A/D829A/D835A/Y1013A; R780A/D829A/D835A/ Y1013A; R783A/D829A/D835A/Y1013A; R765A/D829A/ D835A/N695A; R918A/D829A/D835A/N695A; R895A/ D829A/D835A/N695A; K500A/D829A/D835A/N695A; K929A/D829A/D835A/N695A; R780A/D829A/D835A/ N695A; R783A/D829A/D835A/N695A; N695A/R780A/ R783A/S845D; N695A/R780A/R783A/R832A; N695A/ R780A/R783A/K862A; N695A/R780A/R783A/K866A; N695A/R780A/R783A/R859A; N695A/R780A/R783A/ Q844A; N695A/R780A/R783A/K810A; N695A/R780A/ R783A/K848A; N695A/R780A/R783A/E370A; N695A/ R780A/R783A/E223A; N692A/R780A/R783A/S845D; N692A/R780A/R783A/R832A; N692A/R780A/R783A/ K862A; N692A/R780A/R783A/K866A; N692A/R780A/ R783A/R859A; N692A/R780A/R783A/Q844A; N692A/ R780A/R783A/K810A; N692A/R780A/R783A/K848A; N692A/R780A/R783A/E370A; N692A/R780A/R783A/ E223A; N692A/R780A/N803A/S845D; N692A/R780A/ N803A/R832A; N692A/R780A/N803A/K862A; N692A/ R780A/N803A/K866A, N692A/R780A/N803A/R859A; N692A/R780A/N803A/Q844A; N692A/R780A/N803A/ K810A; N692A/R780A/N803A/K848A; N692A/R780A/ N803A/E370A; N692A/R780A/N803A/E223A; N692A/ R783A/N803A/S845D; N692A/R783A/N803A/R832A; N692A/R783A/N803A/K862A; N692A/R783A/N803A/ K866A; N692A/R783A/N803A/R859A; N692A/R783A/ N803A/Q844A; N692A/R783A/N803A/K810A; N692A/ R783A/N803A/K848A; N692A/R783A/N803A/E370A; N692A/R783A/N803A/E223A; N695A/R783A/N803A/ S845D; N695A/R783A/N803A/R832A; N695A/R783A/ N803A/K862A; N695A/R783A/N803A/K866A; N695A/ R783A/N803A/R859A; N695A/R783A/N803A/Q844A; N695A/R783A/N803A/K810A; N695A/R783A/N803A/ K848A; N695A/R783A/N803A/E370A; N695A/R783A/ N803A/E223A; N695A/R783A/Y812A/S845D; N695A/ R783A/Y812A/R832A; N695A/R783A/Y812A/K862A; N695A/R783A/Y812A/K866A; N695A/R783A/Y812A/ R859A; N695A/R783A/Y812A/Q844A; N695A/R783A/ Y812A/K810A; N695A/R783A/Y812A/K848A; N695A/ R783A/Y812A/E370A; N695A/R783A/Y812A/E223A; K500A/N588A/S845D/Y1013A; K500A/N588A/R832A/ Y1013A; K500A/N588A/K862A/Y1013A; K500A/N588A/ K866A/Y1013A; K500A/N588A/R859A/Y1013A; K500A/ N588A/Q844A/Y1013A; K500A/N588A/K810A/Y1013A; K500A/N588A/K848A/Y1013A; K500A/N588A/E370A/ Y1013A; K500A/N588A/E223A/Y1013A; K500A/N588A/ S845D/Y1013A; N588A/N692A/K1244A/K1246A; R447A/R765A/N497A; R447A/R765A/K929A; R447A/ R765A/N767A; R447A/R765A/N767A/K558A; R447A/ R765A/N767A/R586A; R447A/R765A/N767A/K1244A; R447A/R765A/N767A/K1246A; R447A/R765A/N767A; R447A/N695A/R765A/N767A; R447A/R765A/N695A/ K558A; R447A/R765A/N695A/R586A; R447A/R765A/ N695A/K1244A; R447A/R765A/N695A/K1246A; R447A/ R765A/N767A/K1246A; R447A/N695A/R765A/N767A; R447A/R765A/N695A/K558A; R447A/R765A/N695A/ R586A; R447A/R765A/N695A/K1244A; R447A/R765A/ N695A/K1246A; R447A/N692A/R765A/N767A; R447A/ R765A/N692/K558A; R447A/R765A/N692/R586A; R447A/R765A/N692/K1244A; R447A/R765A/N692/ K1246A; or N14A/R447A/R765A/S845A.

2. The modified Cas9 protein of claim 1, further comprising one or more modification that includes modification of Asn14, Lys268, Glu370, Arg447, Tyr450, Asn497, Lys500, Lys526, Lys528, Lys558, Asn588, Arg661, Asn692, Gln695, Arg780, Arg783, Asn803, Gln805, Lys810, Tyr812, Asp829, Asn831, Arg832, Asp835, Gln844, Lys848, Lys862, Arg925, Gln926, Lys929, His930, Lys961, Lys968, Tyr1013, Lys1031, Lys1244, or Lys1246 corresponding to SEQ ID NO:1.

3. The modified Cas9 protein of claim 2, wherein the modification comprises substitution to an alanine, glycine, lysine, arginine, aspartic acid, or glutamic acid.

4. The modified Cas9 protein of claim 1, wherein the modified Cas9 protein contains at least four amino acid modifications.

5. The modified Cas9 protein of claim 4, wherein the Cas9 modification comprises N14A/R447A/R765A/S845A.

6. The modified Cas9 protein of claim 1, wherein the Cas9 modification comprises: K526A/N588A/R765A/N767A; N588A/K929A/H930A/Y1013A; R447A/K526A/K929A; N588A/N767A/Y1013A/K866A; N588A/N767A/Y1013A/ S845D; K268A/K526A/N588A/N767A; N14A/K526A/ K866A/K1246A; N14A/R447A/Y1013A/K1246A; N588A/ R765A/D835A/K1246A; or N14A/R447A/R765A/S845D.

7. The modified Cas9 protein of claim 1, wherein the Cas9 modification comprises N588A/R765A/D835A/K1246A or N14A/R447A/R765A/S845D.

8. The modified Cas9 protein of claim 1, further comprising a nuclear localization signal, a cell penetrating amino acid sequence, or an affinity tag.

9. The modified Cas9 protein of claim 1, wherein the wild-type Cas9 protein is a *Streptococcus pyogenes* Cas9 protein.

10. A fusion protein comprising the modified Cas9 protein of claim 1 fused to a heterologous peptide or protein, with an optional intervening linker.

11. An expression cassette encoding the modified Cas9 protein of claim 1.

12. An expression vector comprising the expression cassette of claim 11.

13. A host cell expressing the expression cassette of claim 11.

14. A host cell expressing the modified Cas9 protein of claim 1.

15. A method of altering the genome of a cell, the method comprising expressing in the cell or contacting the cell with the modified Cas9 protein of claim 1 linked to a guide RNA having a region complementary to a selected portion of the genome of the cell, resulting in the alteration of the genome of the cell.

16. A method of altering a double stranded DNA (dsDNA) molecule, the method comprising contacting the dsDNA molecule with the modified Cas9 protein of claim 1 linked to a guide RNA having a region complementary to a selected portion of the dsDNA molecule, resulting in the alteration of the dsDNA molecule.

* * * * *